United States Patent
Kim et al.

(10) Patent No.: US 10,396,289 B2
(45) Date of Patent: *Aug. 27, 2019

(54) SPIRO ORGANIC COMPOUNDS, MATERIAL COMPRISING THE SAME FOR ORGANIC ELECTROLUMINESCENCE DEVICES, AND ORGANIC ELECTROLUMINESCENCE DEVICE COMPRISING THE MATERIAL

(71) Applicant: NANJING TOPTO MATERIALS CO., LTD., Nanjing (CN)

(72) Inventors: Jin Woo Kim, Nanjing (CN); Chao Qian, Nanjing (CN); Jun Xu, Nanjing (CN); Dening Wang, Nanjing (CN)

(73) Assignee: NANJING TOPTO MATERIALS CO., LTD., Nanjing (CN)

( * ) Notice: Subject to any disclaimer, the term of this patent is extended or adjusted under 35 U.S.C. 154(b) by 135 days.

This patent is subject to a terminal disclaimer.

(21) Appl. No.: 15/339,141

(22) Filed: Oct. 31, 2016

(65) Prior Publication Data

US 2017/0125677 A1   May 4, 2017

(30) Foreign Application Priority Data

Oct. 30, 2015   (CN) .......................... 2015 1 0732870
Nov. 11, 2015   (CN) .......................... 2015 1 0765354

(51) Int. Cl.
| | | |
|---|---|---|
| H01L 51/00 | (2006.01) | |
| C07C 211/54 | (2006.01) | |
| C07C 211/61 | (2006.01) | |
| H01L 51/50 | (2006.01) | |
| C07D 307/91 | (2006.01) | |
| C07D 209/88 | (2006.01) | |
| C07D 209/86 | (2006.01) | |

(52) U.S. Cl.
CPC .......... H01L 51/006 (2013.01); C07C 211/54 (2013.01); C07C 211/61 (2013.01); C07D 209/86 (2013.01); C07D 209/88 (2013.01); C07D 307/91 (2013.01); H01L 51/0061 (2013.01); C07C 2603/18 (2017.05); C07C 2603/94 (2017.05); C07C 2603/97 (2017.05); H01L 51/0056 (2013.01); H01L 51/0058 (2013.01); H01L 51/0072 (2013.01); H01L 51/0073 (2013.01); H01L 51/0081 (2013.01); H01L 51/5056 (2013.01)

(58) Field of Classification Search
CPC . C07C 13/72; C07C 2103/18; C07C 2103/97; C07C 211/61; C07C 211/54; C07C 2603/95; C07C 2603/96; C07C 2603/97; C07C 2603/18; C07C 2603/93; C07C 2603/94; C07D 209/86; C07D 209/88; C07D 307/91; H01L 51/0052; H01L 51/0056; H01L 51/0058; H01L 51/006; H01L 51/0061; H01L 51/0072; H01L 51/0073; H01L 51/0081; H01L 51/5056
See application file for complete search history.

(56) References Cited

U.S. PATENT DOCUMENTS

| | | |
|---|---|---|
| 2003/0118866 A1 | 6/2003 | Oh et al. |
| 2007/0018569 A1 | 1/2007 | Kawamura et al. |
| 2015/0065730 A1 | 3/2015 | Montenegro et al. |

FOREIGN PATENT DOCUMENTS

| | | |
|---|---|---|
| CN | 1231096 C | 12/2005 |
| CN | 1787988 A | 6/2006 |
| CN | 103664644 A | 3/2014 |
| CN | 104628581 A | 5/2015 |
| CN | 105218302 A | 1/2016 |
| KR | 2015-0030300 A | 3/2015 |

OTHER PUBLICATIONS

Office Action and Search Report dated Sep. 19, 2017, by the State Intellectual Property Office of People's Republic of China in corresponding Chinese Patent Application No. 201510765354.X. (5 pages).

Primary Examiner — Jennifer A Chriss
Assistant Examiner — Elizabeth M. Dahlburg
(74) Attorney, Agent, or Firm — Buchanan Ingersoll & Rooney PC

(57) ABSTRACT

The present invention provides a novel organic compound of General Formula 1, a material comprising the same for organic electroluminescence devices, and an organic electroluminescence device comprising the material. The organic compound of the present invention is useful in organic electroluminescence devices as a hole injection layer substance, a hole transport layer substance, an electron blocking layer substance, and an emission layer substance such as green and red phosphorescent host substance, and when used in the organic electroluminescence devices, can reduce the drive voltage, and increase the luminous efficiency, luminance, thermal stability, color purity and service life of the devices.

[General Formula 1]

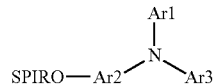

7 Claims, No Drawings

SPIRO ORGANIC COMPOUNDS, MATERIAL COMPRISING THE SAME FOR ORGANIC ELECTROLUMINESCENCE DEVICES, AND ORGANIC ELECTROLUMINESCENCE DEVICE COMPRISING THE MATERIAL

FIELD OF THE INVENTION

The present invention relates to a novel organic compound, a material comprising the same for organic electroluminescence devices, and an organic electroluminescence device comprising the material.

DESCRIPTION OF RELATED ART

Generally speaking, organic electroluminescence is a phenomenon in which electric energy is converted into light energy with the aid of an organic substance. Organic electroluminescence devices utilizing organic electroluminescence generally have a structure including an anode, a cathode and an organic layer sandwiched therebetween. Here, the organic layer is provided for increasing the efficiency and stability of the organic electroluminescence devices, and generally has a multi-layer structure formed with different substances. The multi-layer structure includes, for example, a hole injection layer, a hole transport layer, an emission layer, an electron transport layer, and an electron injection layer, etc.

In the organic electroluminescence devices, the materials used as the organic layer may be classified, according to their functions, into emission materials and charge transport materials, for example, hole injection material, hole transport material, electron transport material, electron injection material and so on.

For the organic electroluminescent device, the most serious problems concerned are their service life and efficiency. With the increase in the dimension of displays, the efficiency and life issues must be addressed.

The efficiency, service life, and drive voltage are correlated with each other. When the efficiency is increased, the drive voltage declines correspondingly. With the decline of the drive voltage, crystallization of the organic substance due to Joule heating occurred upon driving is lowered, resulting in a tendency to life extension.

However, the efficiency of the organic electroluminescent device cannot be maximized by simply improving the organic layer, since when an optimized combination of the energy level, the T1 value, and the intrinsic characteristics (mobility, and interface characteristics, etc.) of the organic layers is formed, long life and high efficiency cannot be achieved at the same time.

As a hole transport layer substance in the organic electroluminescence device, aromatic amine is used. This is because generally the efficacy of a variety of amines is disclosed in the prior art, in terms of the improvement of the performance of the organic electroluminescence devices. For the hole transport substance, the improved factors include higher hole transport mobility, more amorphous structure, higher glass transition temperature, and higher electronic chemical stability. The organic electroluminescence devices fabricated by using such amines with improved performances in various aspects are also improved in the performances in various aspects, such as, higher luminous efficiency, extended shipping and storage life, and more excellent thermal resistance. For example, in U.S. Pat. No. 5,061,569 issued to Van et al, an improved arylamine as a hole transport substance is disclosed. In U.S. Pat. No. 5,554,450 issued to Shi et al., a series of aromatic amines are disclosed which are designed for high-temperature resistant organic electroluminescence devices and have a high glass transition temperature of about 165° C. In U.S. Pat. No. 5,374,489 issued to Shirota et al., stable amorphous glass is disclosed, which is a novel π-conjugated stellar m-MTDATA acting as an excellent hole transport substance.

In the hole transport layer in an organic electroluminescence device, generally no other organic compounds than aromatic amines are used, and the hole transport characteristic of aromatic amines are generally accepted. However, when the aromatic amines are used as a hole transport layer in a two-layer organic electroluminescence device, a vital defect exists. Because amines are generally a strong electron donor, they interact with a light emitting substance used in the electron transport layer to form a fluorescence quenching center, thus reducing the luminous efficiency of the organic electroluminescence device.

Moreover, in recent organic electroluminescence devices, it is necessary to provide a light-emitting auxiliary layer between the hole transport layer and the emission layer, to solve the problem of light emitting in the hole transport layer. At present, there is a need for developing a light-emitting auxiliary layer according to the difference of the respective emission layers (R, G, and B).

Generally, electrons are passed from the electron transport layer to the emission layer, and the holes are passed from the hole transport layer to the emission layer. Then, they are recombined to form excitons.

However, the substances used in the hole transport layer needs to have a low HOMO value and thus generally have a low T1 value. As a result, the excitons generated in the emission layer flow to the hole transport layer, causing unbalanced charges in the emission layer and light emitting in or at the interface of the hole transport layer. This leads to low color purity and decreased efficiency and service life of the organic electroluminescence device.

Moreover, a substance having a high hole mobility may be used to reduce the drive voltage. However, the hole mobility is faster than the electron mobility, which causes unbalanced charges in the emission layer, and thus causes the occurrence of low color purity and efficiency and shortened service life of the organic electroluminescence devices.

Therefore, there is an urgent need for developing a light-emitting auxiliary layer that has a high T1 value and a HOMO energy level ranging between the HOMO energy level of the hole transport layer and the HOMO energy level of the emission layer.

Furthermore, there is a need for developing a hole injection layer material having a high glass transition temperature, which can solve one of the causes to shortened service life of the organic electroluminescence device by delaying the diffusion of a metal compound from the anode electrode (ITO) to the organic layer, and is highly stable with respect to Joule heating occurred during driving the device. Where the glass transition temperature of the hole transport layer material is low, the surface evenness of the thin film is caused to decrease when the device is driven. This problem is reported to have a high impact on the service life of the device. Moreover, the organic electroluminescence device is mainly formed by deposition. Therefore, there is a need at present for developing a plating tolerant material, that is, a strongly thermal resistant material.

To exert the aforesaid excellent properties of the organic electroluminescence device fully, the substance for forming an organic layer in the device, for example, the hole injection substance, the hole transport substance, the emission substance, the electron transport substance, the electron injection substance, and so on, should be a stable and high-efficiency material. However, no stable and high-efficiency organic materials for organic electroluminescence devices are well developed at present. Therefore, there is a persistent need in the art for developing novel materials with low drive voltage, high efficiency, and long life.

LITERATURES

Patent Document

South Korea Laid-Open Patent Publication No: 10-2011-0103141

SUMMARY OF THE INVENTION

Technical Problem

An objective of the present invention is to provide a novel organic compound, which can be used in organic electroluminescence devices as a hole injection layer substance, a hole transport layer substance, an electron blocking layer substance, or an emission layer substance, and functions to lower the drive voltage, and increase the luminous efficiency, luminance, thermal stability, color purity, and service life of the devices.

Another objective of the present invention is to provide a hole injection layer material, a hole transport layer material, an electron blocking layer material, and an emission layer material comprising the novel organic compound.

A further objective of the present invention is to provide an organic electroluminescence device using the novel organic compound.

Means to Solve the Problem

The present invention provides a novel organic compound represented by General Formula 1 below:

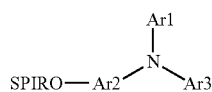

[General Formula 1]

where Ar1 and Ar3 are the same or different in each case, and are an aromatic or heteroaromatic ring system having 6 to 60 carbon atoms selected from the group consisting of benzene, biphenyl, naphthalene, phenanthrene, fluorene, dibenzofuran, dibenzothiophene (each of which may be substituted with one or more radicals R5), substituted or unsubstituted spirobifluorene, or a combination of 2, 3, 4, or 5 thereof (which are the same or different in each case);

Ar2 is a heteroaromatic ring system having 6 to 60 carbon atoms selected from the group consisting of benzene, biphenyl, naphthalene, phenanthrene, fluorene, spirobifluorene, dibenzofuran, and dibenzothiophene (each of which may be substituted with one or more radicals R5);

R5 is the same or different in each case, and is one selected from the group consisting of H, D, F, Cl, Br, I, CN, Si(R2)$_3$, a linear alkyl, alkoxy or thioalkyl having 1 to 31 carbon atoms or a branched alkyl or cycloalkyl, alkoxy, or thioalkyl having 3 to 31 carbon atoms, an aromatic or heteroaromatic ring system having 6 to 60 carbon atoms selected from the group consisting of benzene, naphthalene, phenanthrene, fluorene, spirobifluorene, dibenzofuran, dibenzothiophen or a combination of 2, 3, 4, or 5 thereof (which are the same or different in each case), an aryloxy having 5 to 40 aromatic ring atoms, or an aralkyl having 5 to 40 aromatic ring atoms; and R5 are the same or different in each case;

SPIRO is a compound of General Formula 2 below:

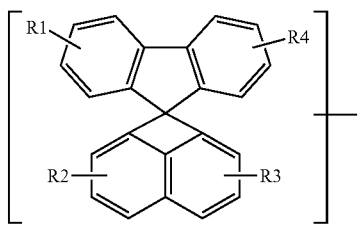

[General Formula 2]

where in General Formula 2

R1, R2, R3, and R4 are the same or different in each case, and are selected from H, D, F, Cl, Br, I, CN, Si(R)$_3$, a linear alkyl, alkoxy or thioalkyl having 1 to 40 carbon atoms or a branched alkyl or cycloalkyl, alkoxy, or thioalkyl having 3 to 40 carbon atoms, an aromatic or heteroaromatic ring system having 6 to 60 carbon atoms selected from the group consisting of benzene, naphthalene, phenanthrene, fluorene, spirobifluorene, dibenzofuran, dibenzothiophen, or a combination of 2, 3, 4, or 5 thereof (which are the same or different in each case), an aryloxy having 5 to 60 aromatic ring atoms, or an aralkyl having 5 to 60 aromatic ring atoms.

The present invention provides a hole injection layer material, a hole transport layer material, an electron blocking layer material, and an emission layer material comprising the organic compound of General Formula 1.

Moreover, the present invention relates to an organic electroluminescence device, which has one or more organic thin film layers, including at least an emission layer, deposited between a cathode and anode, in the organic electroluminescence device. At least one or more of the organic thin film layers contains one or a combination of two or more of the organic compounds of General Formula 1. The present invention relates to organic electroluminescence devices characterized as described above.

Beneficial Effect

The organic compound according to the present invention can be used in organic electroluminescence devices as a hole injection layer substance, a hole transport layer substance, an electron blocking layer substance, and an emission layer substance such as green and red phosphorescent host substance, and when used in the organic electroluminescence devices, can reduce the drive voltage, and increase the luminous efficiency, brightness, thermal stability, color purity and service life of the devices.

Furthermore, the organic electroluminescence device fabricated by using the organic compound of the present invention has the characteristics of high efficiency and long service life.

DETAILED DESCRIPTION

The present invention relates to a novel compound represented by General Formula 1 below:

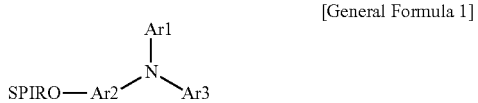
[General Formula 1]

where Ar1 and Ar3 are the same or different in each case, and are an aromatic or heteroaromatic ring system having 6 to 60 carbon atoms selected from the group consisting of benzene, biphenyl, naphthalene, phenanthrene, fluorene, dibenzofuran, dibenzothiophene (each of which may be substituted with one or more radicals R5), substituted or unsubstituted spirobifluorene, or a combination of 2, 3, 4, or 5 thereof (which are the same or different in each case);

Ar2 is a heteroaromatic ring system having 6 to 60 carbon atoms selected from the group consisting of benzene, biphenyl, naphthalene, phenanthrene, fluorene, spirobifluorene, dibenzofuran, and dibenzothiophene (each of which may be substituted with one or more radicals R5);

R5 is the same or different in each case, and is one selected from the group consisting of H. D, F, Cl, Br, I, CN, $Si(R)_3$, a linear alkyl, alkoxy or thioalkyl having 1 to 31 carbon atoms or a branched alkyl or cycloalkyl, alkoxy, or thioalkyl having 3 to 31 carbon atoms, an aromatic or heteroaromatic ring system having 6 to 60 carbon atoms selected from the group consisting of benzene, naphthalene, phenanthrene, fluorene, spirobifluorene, dibenzofuran, dibenzothiophen, or a combination of 2, 3, 4, or 5 thereof (which are the same or different in each case), an aryloxy having 5 to 40 aromatic ring atoms, or an aralkyl having 5 to 40 aromatic ring atoms; and SPIRO is a compound represented by General Formula 2 below:

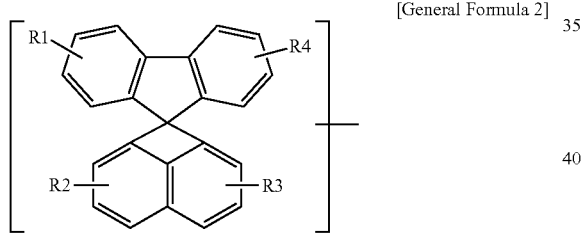
[General Formula 2]

where

R1, R2, R3, and R4 are the same or different in each case, and are selected from H, D, F, Cl, Br, I, CN, $Si(R)_3$, a linear alkyl, alkoxy or thioalkyl having 1 to 40 carbon atoms or a branched alkyl or cycloalkyl, alkoxy, or thioalkyl having 3 to 40 carbon atoms, an aromatic or heteroaromatic ring system having 6 to 60 carbon atoms selected from the group consisting of benzene, naphthalene, phenanthrene, fluorene, spirobifluorene, dibenzofuran, dibenzothiophen, or a combination of 2, 3, 4, or 5 thereof (which are the same or different in each case), an aryloxy having 5 to 60 aromatic ring atoms, or an aralkyl having 5 to 60 aromatic ring atoms.

In General Formulas 1 and 2,

Ar1 and Ar3 are the same or different in each case, and are an aromatic or heteroaromatic ring system having 6 to 31 carbon atoms selected from the group consisting of benzene, naphthalene, phenanthrene, fluorene, dibenzofuran, dibenzothiophene (each of which may be substituted with one or more radicals R5), and substituted or unsubstituted spirobifluorene;

Ar2 is a heteroaromatic ring system having 6 to 31 carbon atoms selected from the group consisting of benzene, naphthalene, phenanthrene, fluorene, spirobifluorene, dibenzofuran, and dibenzothiophene (each of which may be substituted with one or more radicals R5);

R1, R2, R3, R4, and R5 are the same or different in each case, and are selected from H, D, F, Cl, Br, I, CN, $Si(R)_3$, a linear alkyl, alkoxy or thioalkyl having 1 to 25 carbon atoms or a branched alkyl or cycloalkyl, alkoxy, or thioalkyl having 3 to 25 carbon atoms, an aromatic or heteroaromatic ring system having 6 to 31 carbon atoms selected from the group consisting of benzene, naphthalene, phenanthrene, fluorene, spirobifluorene, dibenzofuran, and dibenzothiophen, an aryloxy having 5 to 31 aromatic ring atoms, or an aralkyl having 5 to 31 aromatic ring atoms.

Specifically, the organic compound may be any one of Compounds 1 to 49:

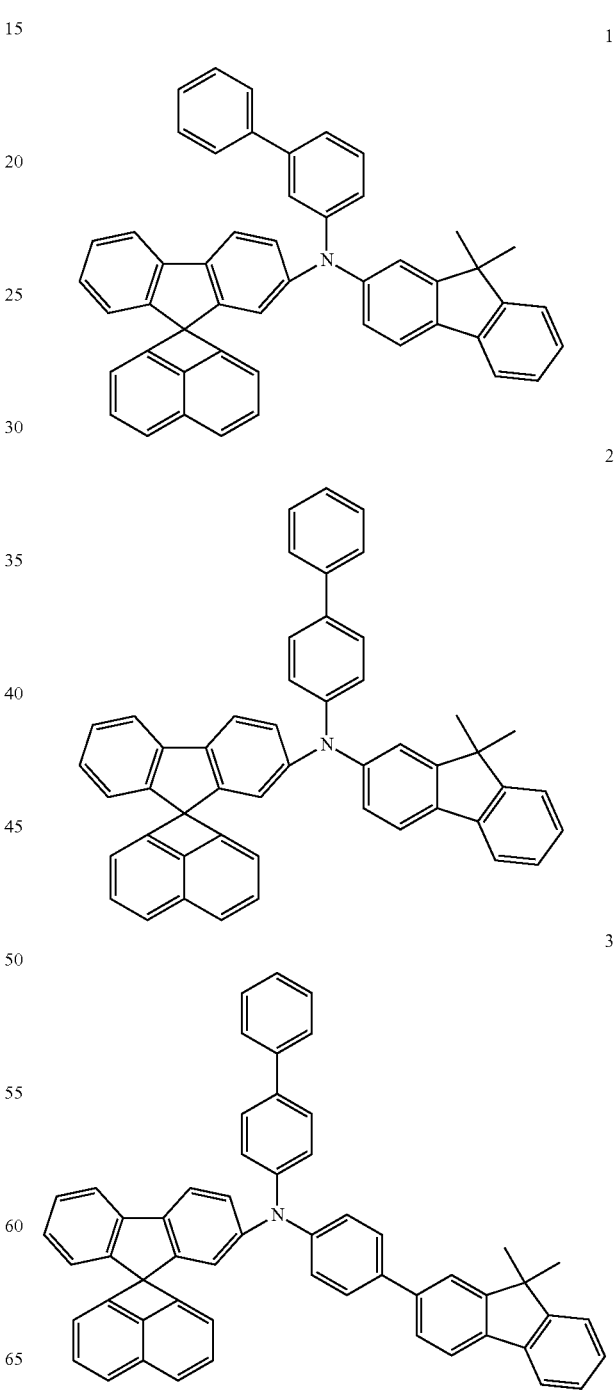

4
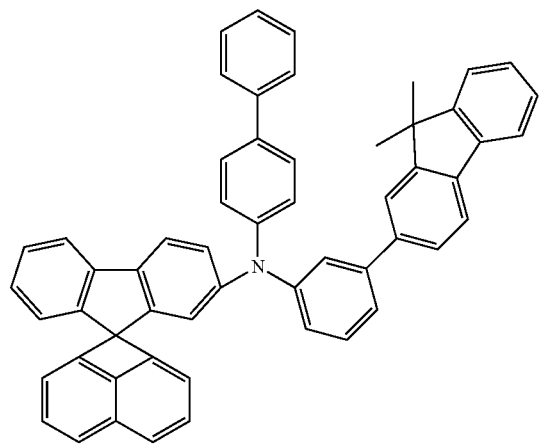
5
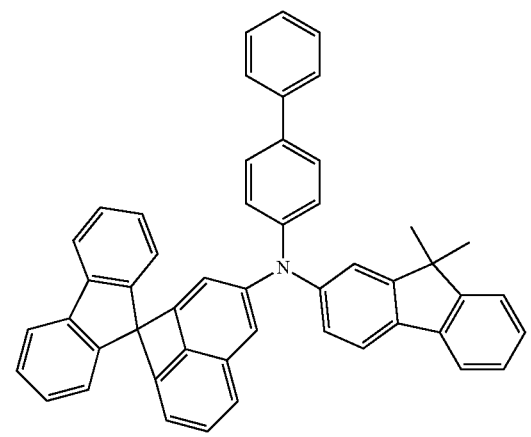
6
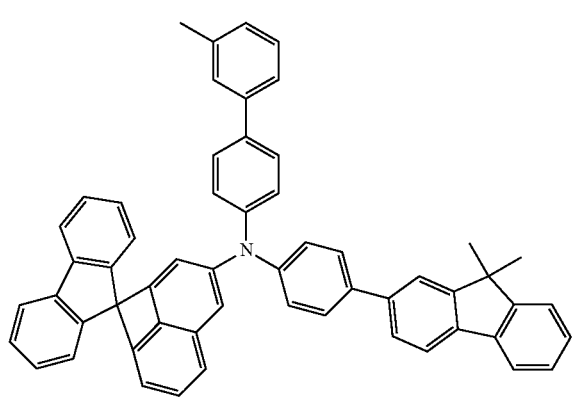
5
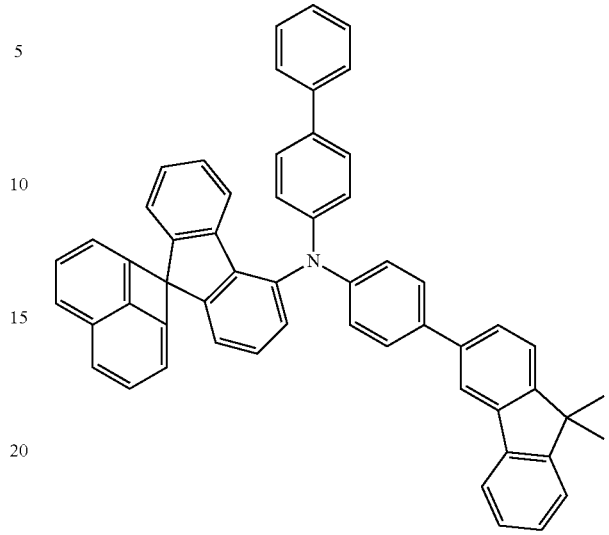
8
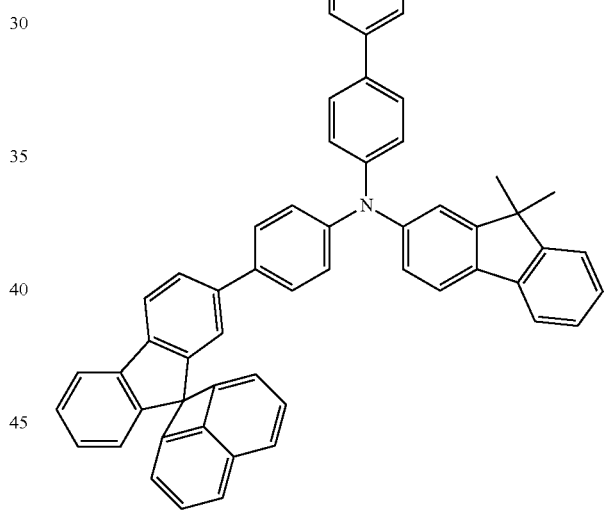
9
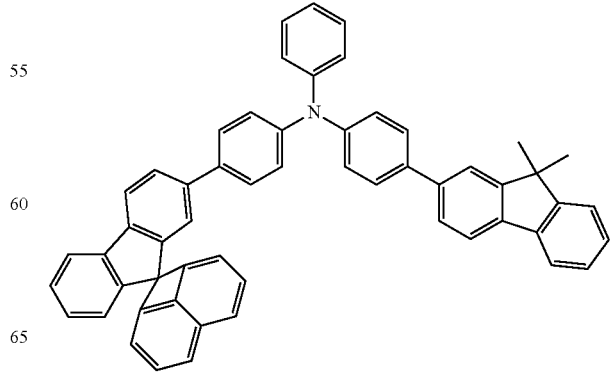

10
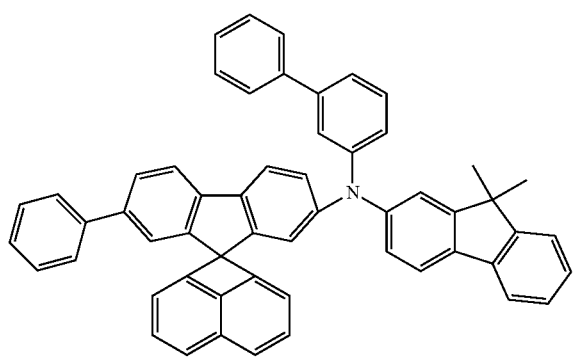
11
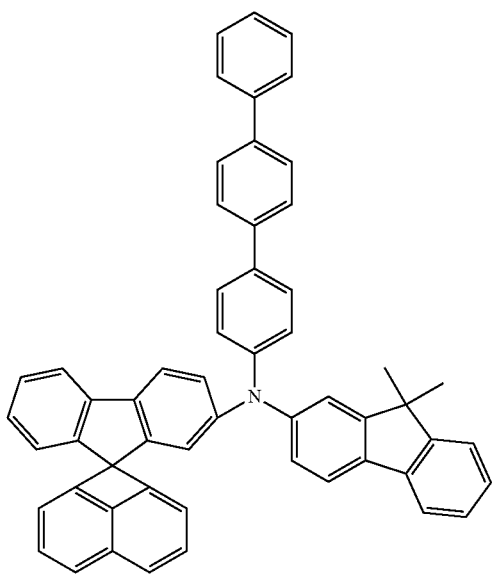
12
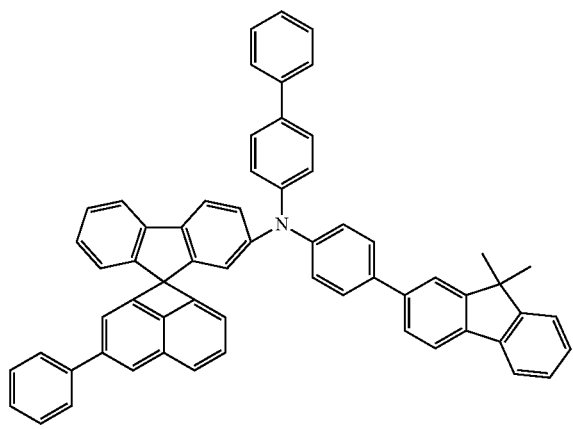
13
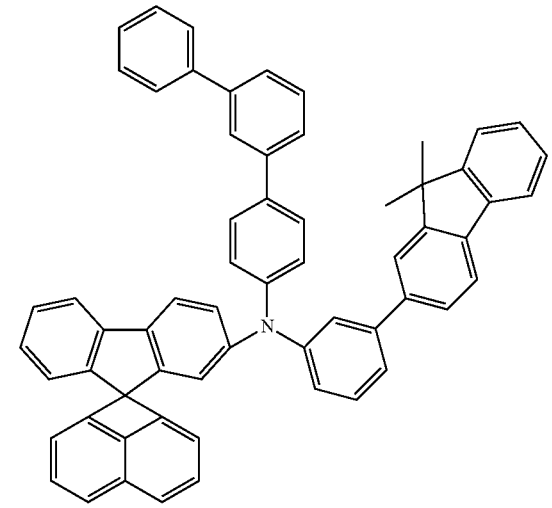
14
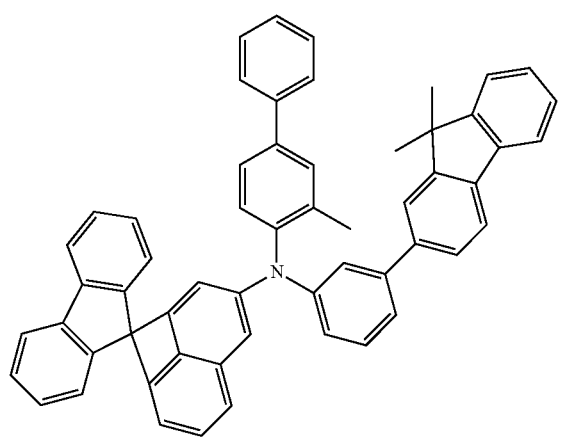
15
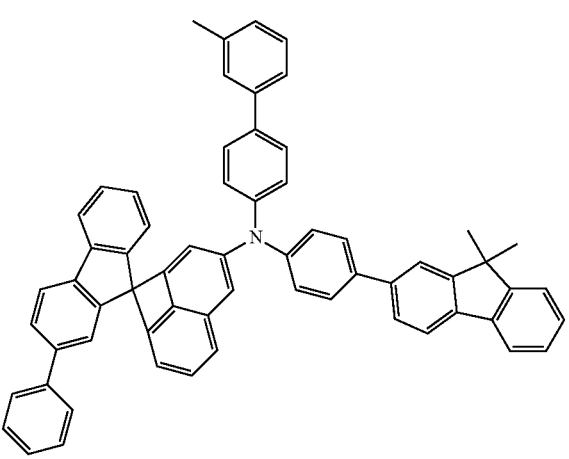

16
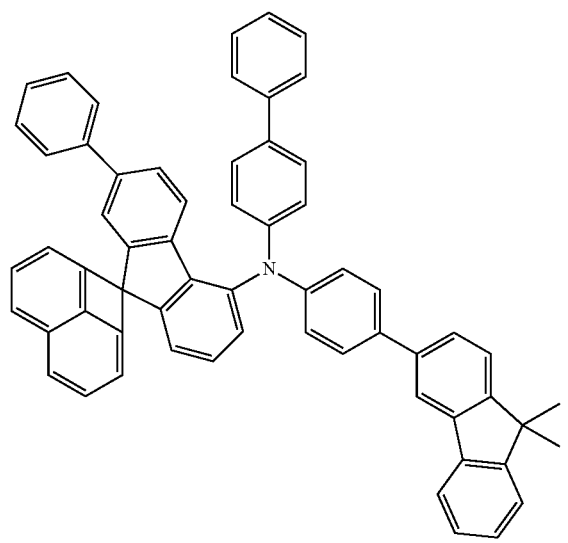
17
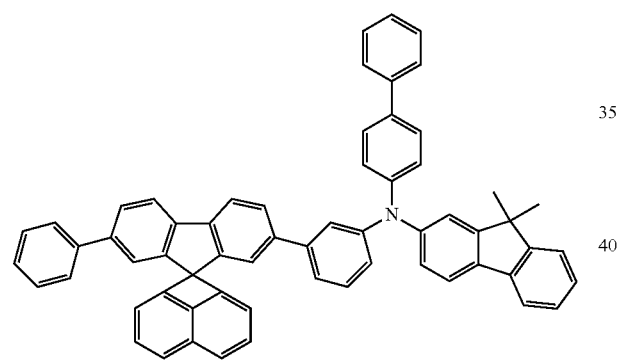
18
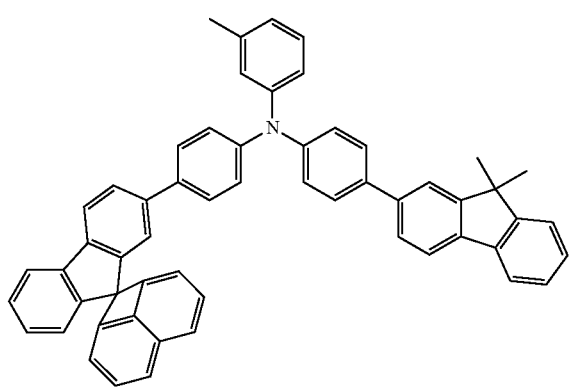
19
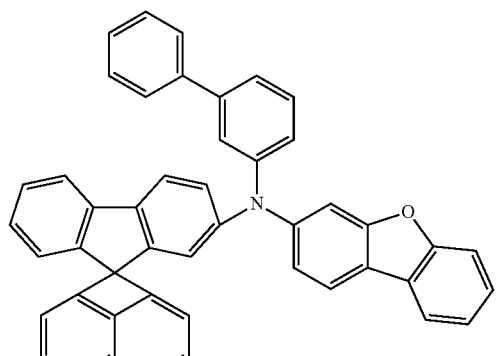
20
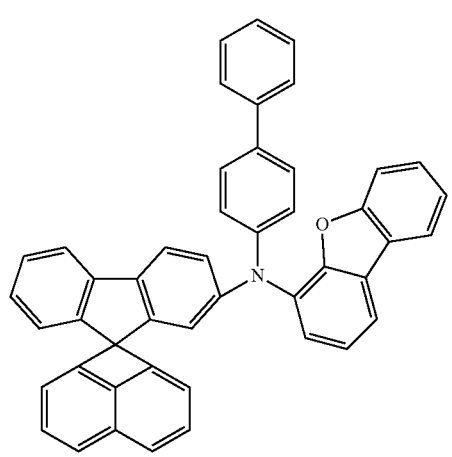
21
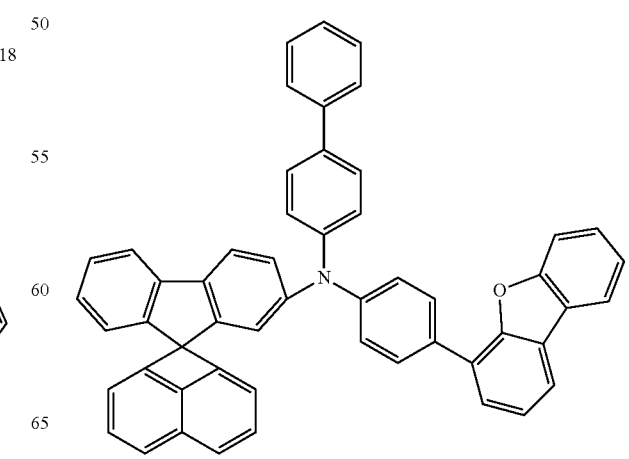

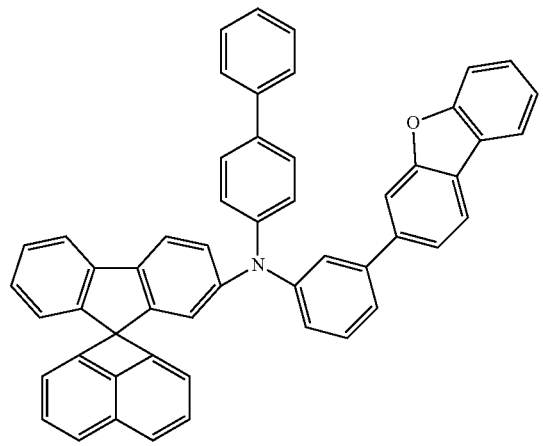
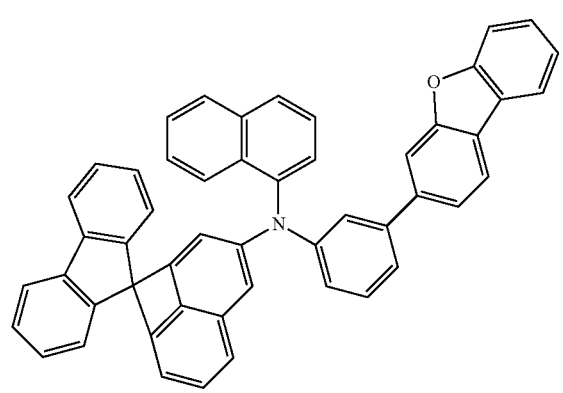
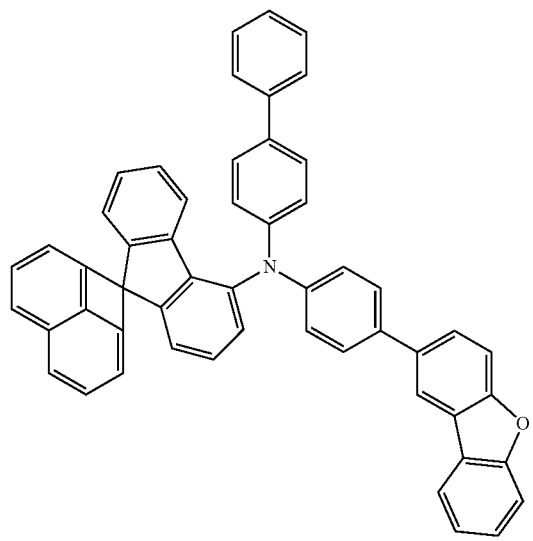
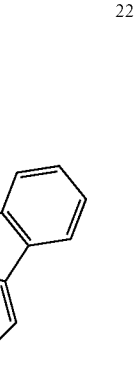
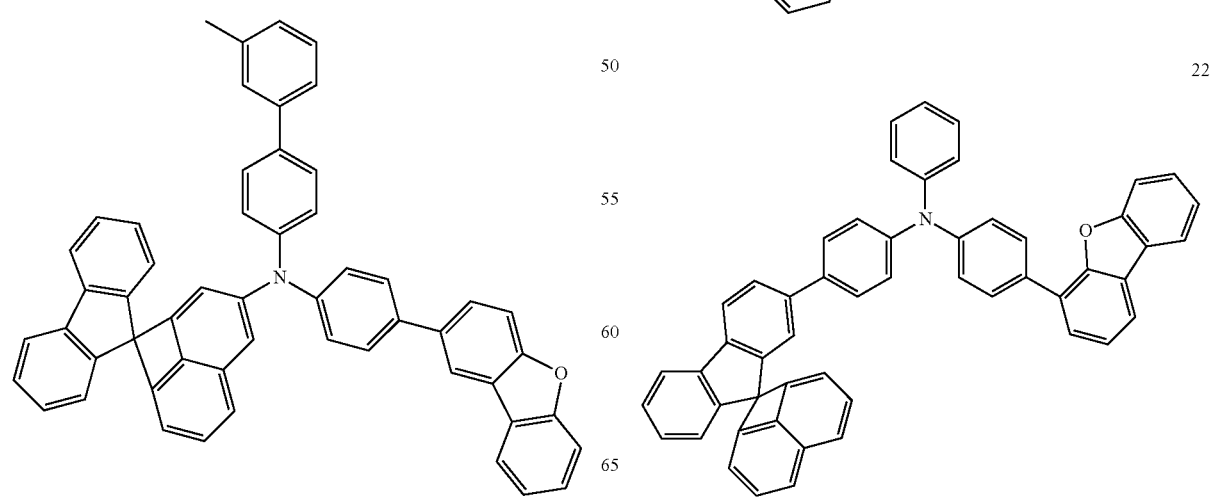

28
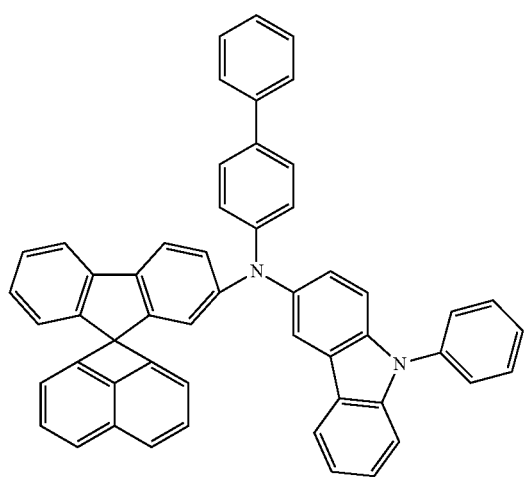
29
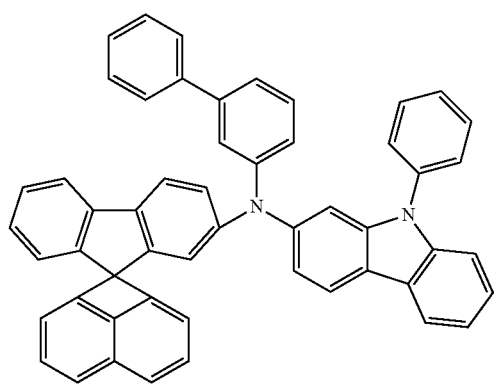
30
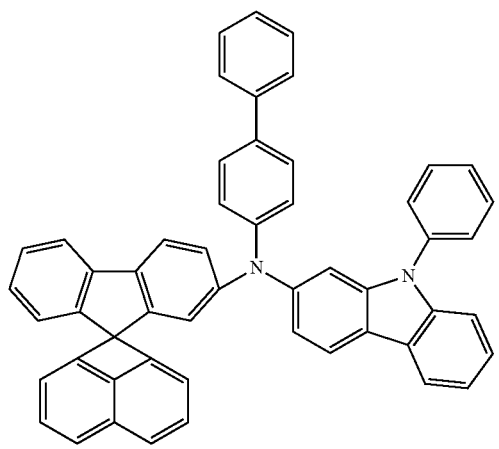
31
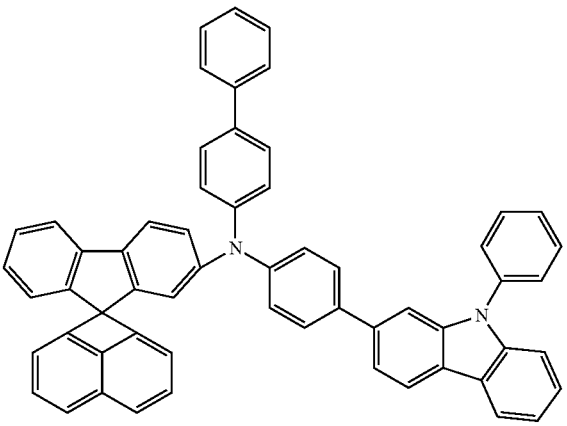
32
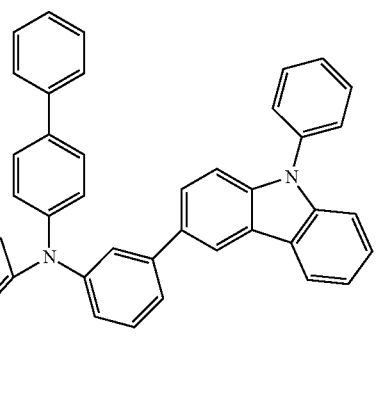
33
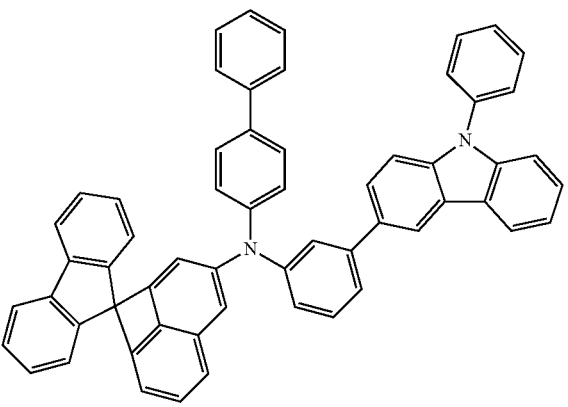

34
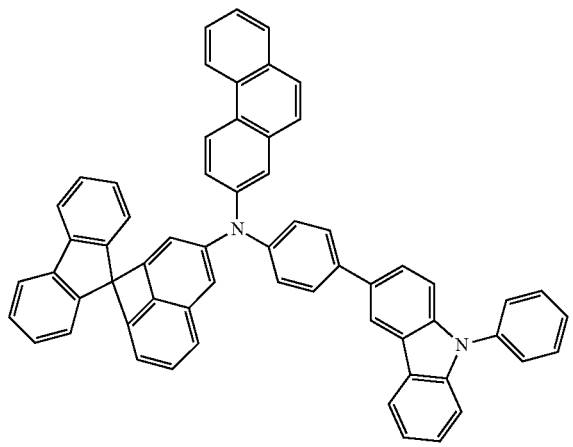
35
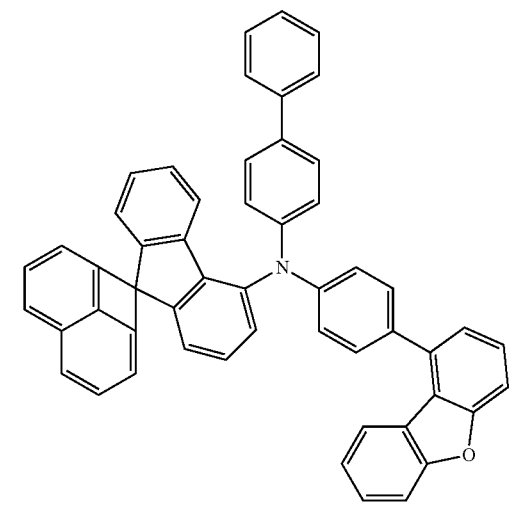
36
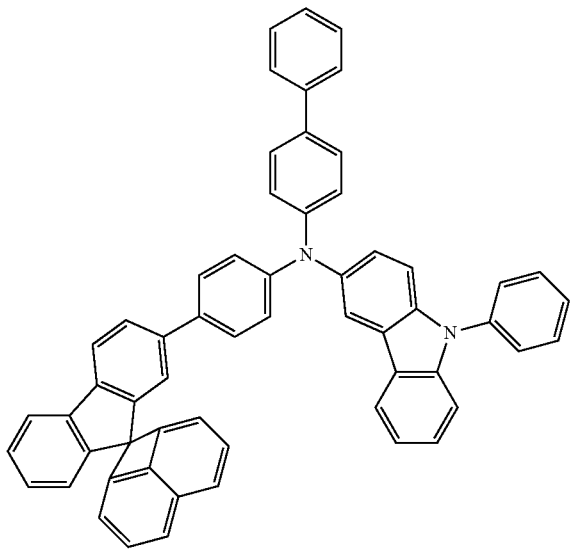
37
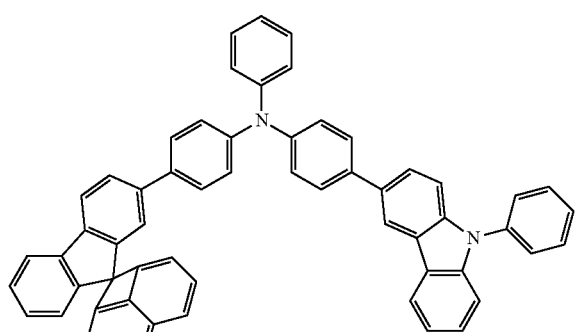
38
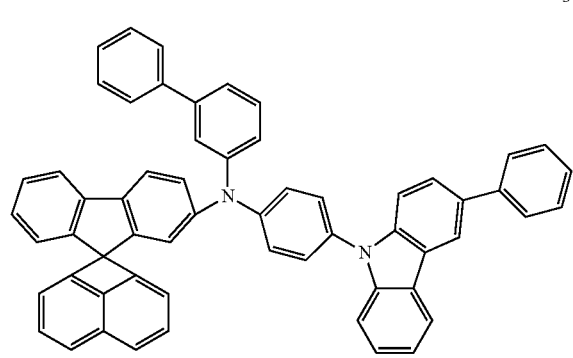
39
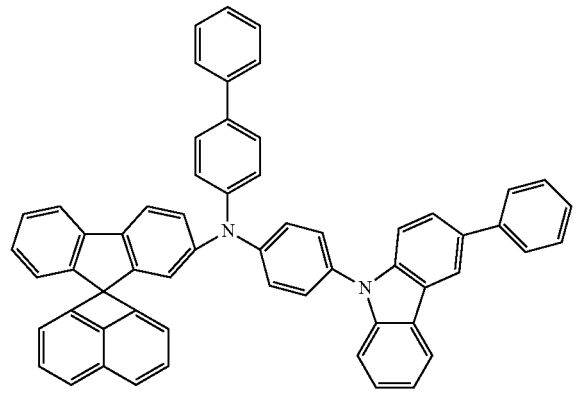
40
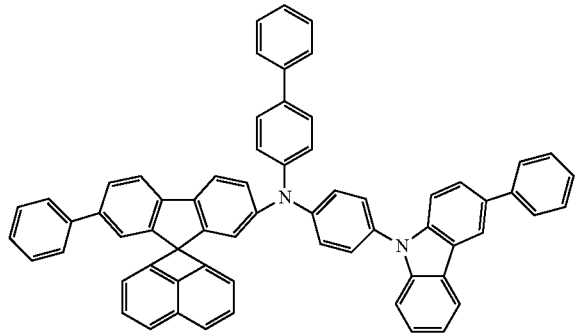

41
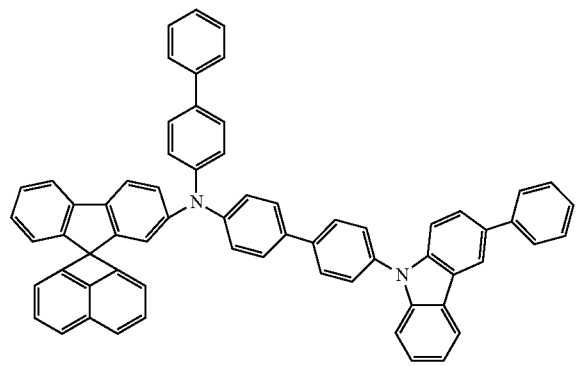
42
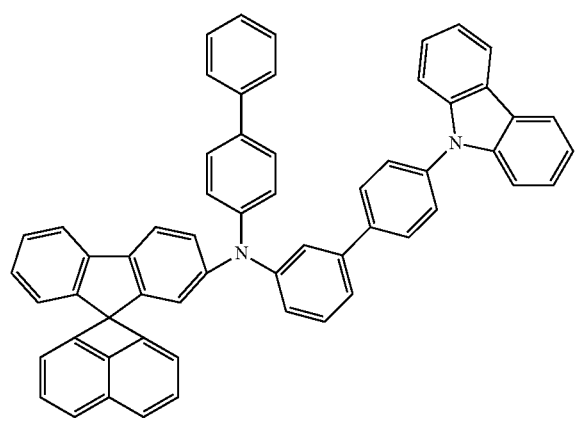
43
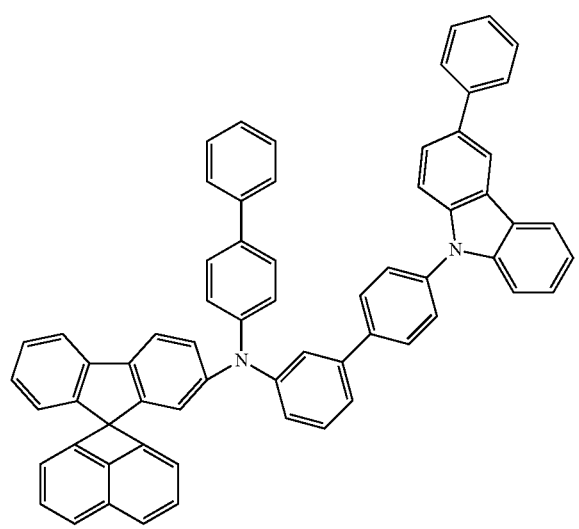
44
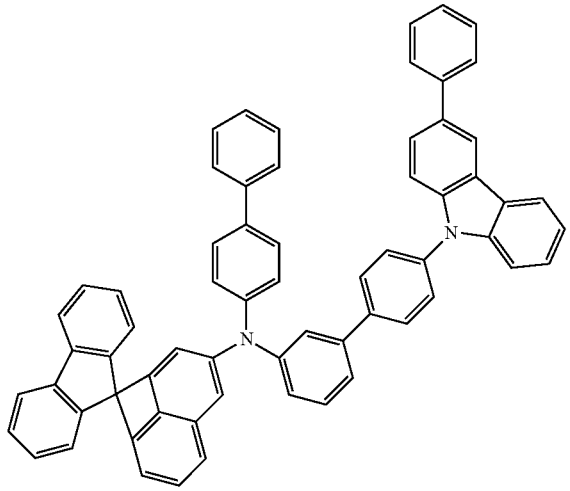
45
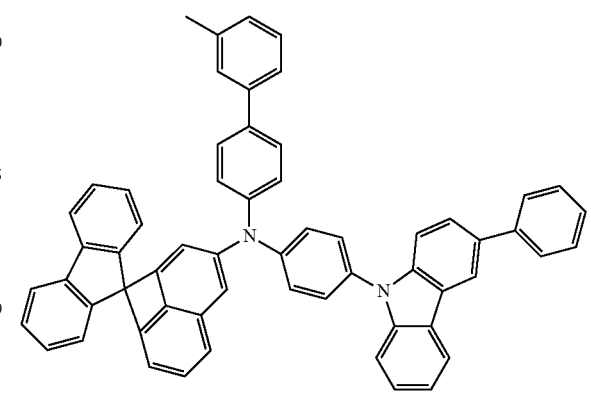
46
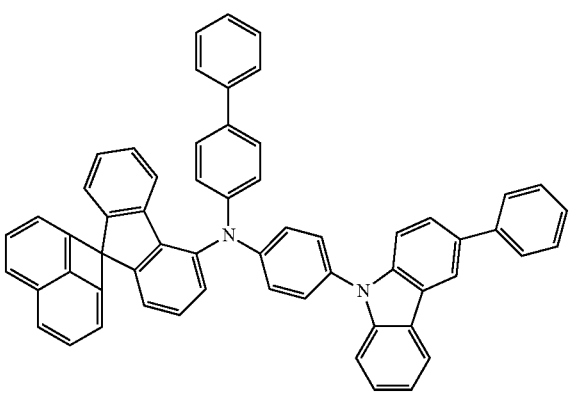

47

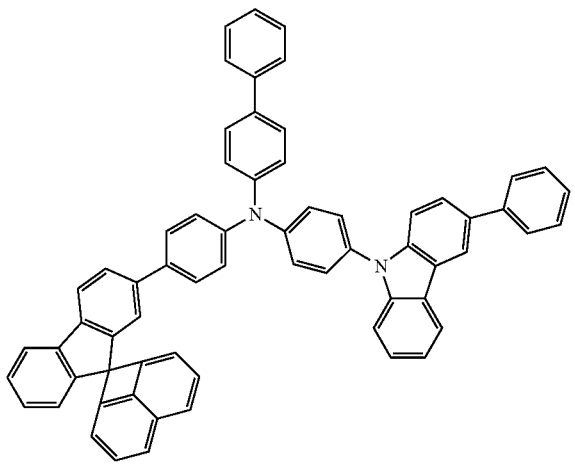

48

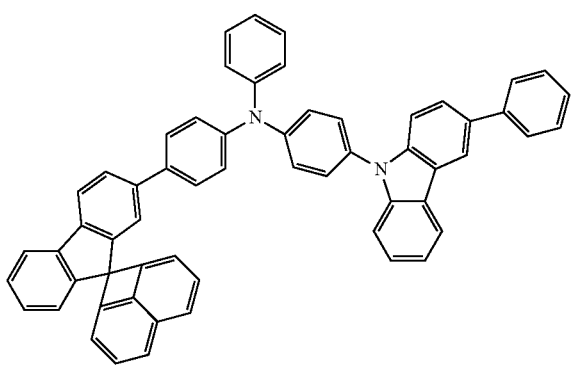

49

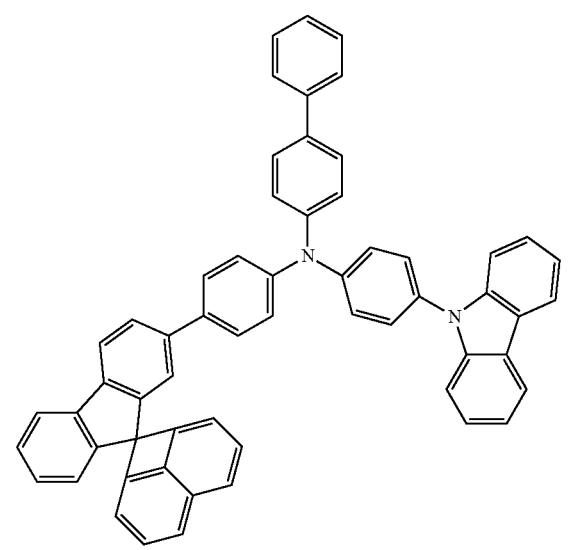

The organic compound provided in the present invention can be used in organic electroluminescence devices as a hole injection layer material, a hole transport layer material, an electron blocking layer material, or an emission layer material. For example, the emission layer material may be a green or red phosphorescent host material.

Furthermore, the present invention also relates to a hole injection layer material, a hole transport layer material, an electron blocking layer material, or an emission layer material comprising the organic compound above.

For facilitating the formation of the hole injection layer, the hole transport layer, the electron blocking layer, and the emission layer, during fabrication, the hole injection layer material, the hole transport layer material, the electron blocking layer material, and the emission layer material can not only be in various states, for example liquid state, but also added with commonly used substances.

Moreover, the present invention further relates to an organic electroluminescence device, which has one or more organic thin film layers, including an emission layer, deposited between an anode and a cathode. At least one of the organic thin film layers contains one or a combination of two or more of the organic compounds of General Formula 1.

At least one of the hole injection layer material, the hole transport layer material, the electron blocking layer material, and the emission layer material of the organic electroluminescence device contains the organic compound of General Formula 1.

The organic electroluminescence device has a structure where the anode, a hole injection layer, a hole transport layer, the emission layer, an electron transport layer, an electron injection layer, and the cathode are laminated. Optionally, an electron blocking layer and a hole blocking layer may be added.

The organic thin film layers include a hole injection layer, a hole transport layer, the emission layer, an electron transport layer, and an electron injection layer, and the organic compound of General Formula 1 is contained in at least one of the hole injection layer, the hole transport layer, and the emission layer.

Hereinafter, the organic electroluminescence device of the present invention is described by way of examples. However, the organic electroluminescence device of the present invention is not limited thereto.

The organic electroluminescence device of the present invention has a structure comprising the anode (hole injection electrode), a hole injection layer (HIL), a hole transport layer (HTL), the emission layer (EML), and the cathode (electron injection electrode) laminated in sequence. If possible, an electron blocking layer (EBL) may be added between the anode and the emission layer, and a hole blocking layer (HBL) may be added between the cathode and the emission layer.

The organic electroluminescence device of the present invention is fabricated by a process comprising the following steps.

Step 1: An anode material is laminated through a conventional process on a surface of a substrate to form an anode. The substrate used is a glass or transparent plastic substrate having good penetrability, surface smoothness, operability, and waterproof performance. Furthermore, the anode material may be transparent and highly conductive indium tin oxide (ITO), indium zinc oxide (IZO), tin dioxide ($SnO_2$), and zinc oxide (ZnO) etc.

Step 2: A hole injection layer (HIL) material is applied onto a surface of the anode through a conventional process by vacuum deposition or by spin coating, to form a hole injection layer. Here, the hole injection layer material may be, in addition to the organic compound of the present invention, for example, CuPc, m-MTDATA, m-MTDAPB, and starburst amines TCTA, 2-TNATA, or IDE406 commercially available from Idemitsu Kosan Co., Ltd.

Step 3: A hole transport layer (HTL) material is applied onto a surface of the hole injection layer through a conventional process by vacuum thermal deposition or by spin coating, to form a hole transport layer. Here, the hole transport layer material may be, in addition to the organic compound of the present invention, α-NPD, NPB, or TPD.

Step 4: An emission layer (EML) material is applied onto a surface of the hole transport layer through a conventional process by vacuum thermal deposition or by spin coating, to form an emission layer. Here, the emission layer substance may be the organic compound of the present invention, $Alq_3$, and the like, when the sole light-emitting substance or light emitting host substance is green; and may be Balq (bis(8-hydroxyquinolinato) beryllium), DPVBi series, spiro substance, spiro-DPVBi, LiPBO, bis(biphenylvinyl)benzene, aluminium-quinoline metal comlex, and compexes of imidazole, thiazole, and oxadiazole with metals, when the sole light-emitting substance or light emitting host substance is blue. The organic compound of the present invention may be used as a red phosphorescent host substance.

Further, the emission layer substance may include a dopant used with the light emitting host, and the florescent dopant may be IDE102 and IDE105 commercially available from Idemitsu Kosan Co., Ltd; and the phosphorescent dopant may be Ir(ppy)3, FIrpic (see [Chihaya Adachi et al., Appl. Phys. Lett., 2001, 79, 3082-3084]), PtOEP, and TBE002.

Further, an electron blocking layer (EBL) may be added between the hole transport layer and the emission layer.

Step 5: An electron transport layer (ETL) material is applied onto a surface of the emission layer through a conventional process by vacuum thermal deposition or by spin coating, to form an electron transport layer. The electron transport layer material is not particularly limited, and preferably $Alq_3$.

Further, a hole blocking layer (HBL) may also be added between the emission layer and the electron transport layer, which, in combination with the use of a phosphorescent dopant in the emission layer, can prevent the triplet excitons or hole from diffusing into the electron transport layer.

A hole blocking layer (HBL) material is applied onto a surface of the emission layer through a conventional process by vacuum thermal deposition or by spin coating, to form a hole blocking layer. The hole blocking layer material is not particularly limited, which may be, in addition to the organic compound of General Formula 1 of the present invention, Liq, bis(2-methyl-8-quinolinolato)-(1,1'-Biphenyl-4-olato) aluminum, BCP, and LiF etc.

Step 6: An electron injection layer (EIL) material is applied onto a surface of the electron transport layer through a conventional process by vacuum thermal deposition or by spin coating, to form an electron injection layer. The electron injection layer substance may be LiF, Liq, $Li_2O$, BaO, NaCl, CsF, and so on.

Step 7: A cathode material is applied onto the electron injection layer through a conventional process by vacuum thermal deposition or by spin coating, to form a cathode.

The cathode material may be Li, Al, Al—Li, Ca, Mg, Mg—In, Mg—Ag, and the like. Furthermore, for the organic electroluminescence devices, a light penetrable transparent cathode can be fabricated when indium tin oxide (ITO) or indium zinc oxide (IZO) is used.

According to the composition of the overlay above, a capping layer (CPL) may be further formed on a surface of the cathode.

Hereinafter, methods for synthesizing the compounds of General Formula 1 are described by way of representative examples. However, the methods for synthesizing the compounds of the present invention are not limited to those exemplified below, and the compounds of the present invention may be prepared through the methods exemplified below and methods generally known in the art.

Preparation Process 1: Compound Synthesis

Synthesis of Intermediates 1 and 2

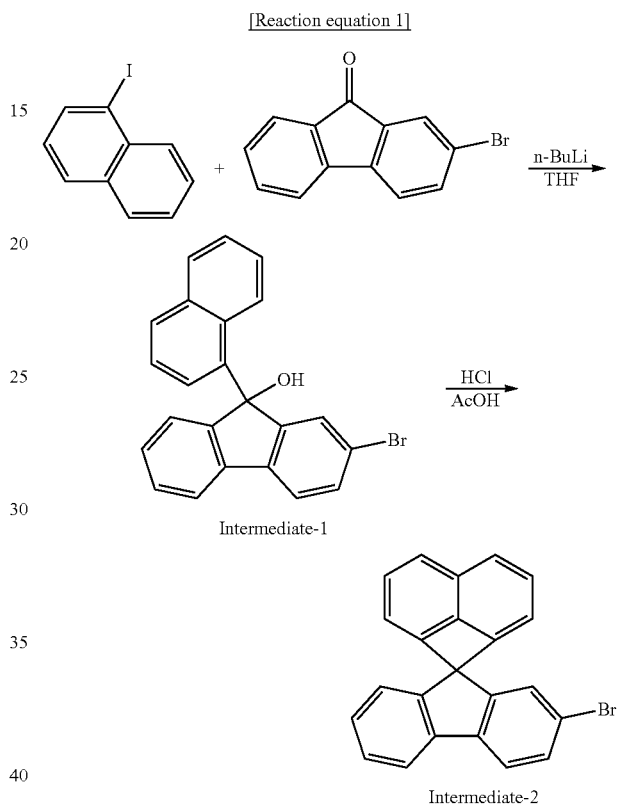

Intermediate-1

Intermediate-2

1-iodonaphthalene (2.54 g, 10 mmol) was dissolved in tetrahydrofuran (15 mL) and cooled to −78° C. n-butyllithium (2.5 M, 4 mL) was added dropwise, and stirred at −78° C. for 1 hr. 2-bromo-9-fluorenone (2.59 g, 10 mmol) dissolved in tetrahydrofuran (30 mL) was slowly added dropwise, and warmed to normal temperature. After the reaction was terminated, MC and 2N HCl were added, and the organic layer was extracted.

The organic layer was dried over anhydrous magnesium sulfate, suctioned, and concentrated. The resultant compound was purified by column chromatography eluting with Hex:EA=5:1, to obtain Intermediate 1 (3.06 g, 79%).

Intermediate 1 was dissolved in acetic acid, and then concentrated hydrochloric acid was added dropwise, and refluxed for 1 hr. The reaction was terminated, and extracted with diethyl ether and water. The organic layer was washed with a saturated sodium bicarbonate solution in water, dried over magnesium sulfate, recrystallized, and purified by column chromatography eluting with Hex:EA=5:1, to obtain Intermediate 2 (2.99 g, 81%).

Intermediate 1 MS(FAB): 387 ($M^+$)

Intermediate 2 MS(FAB): 369 ($M^+$)

Synthesis of Intermediates 3 and 4

[Reaction equation 2]

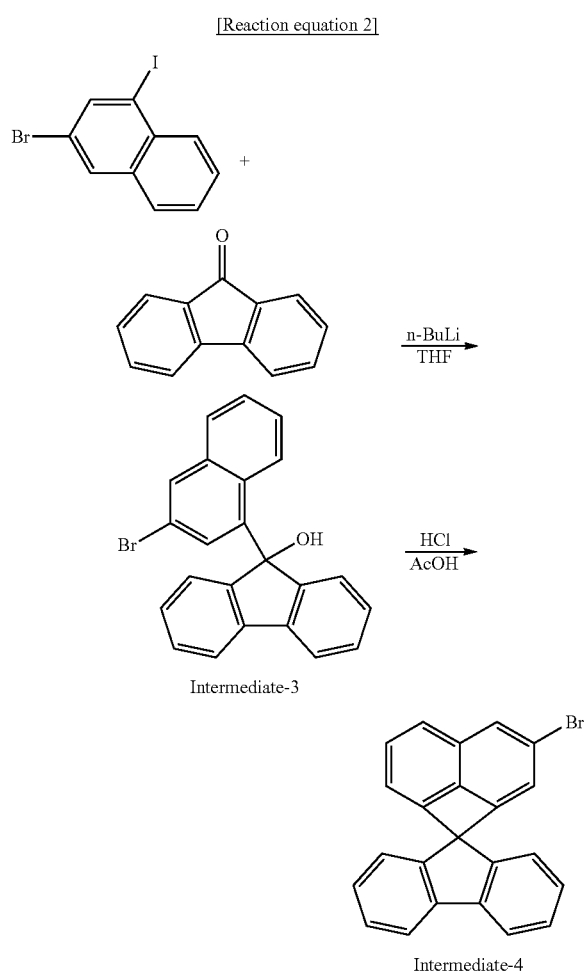

Intermediate-3

Intermediate-4

3-bromo-1-iodonaphthalene (3.33 g, 10 mmol) was dissolved in tetrahydrofuran (15 mL), and then cooled to −78° C. n-butyllithium (2.5 M, 4 mL) was added dropwise and stirred at −78° C. for 1 hr. 9H-fluorenone (1.80 g, 10 mmol) dissolved in tetrahydrofuran (30 mL) was slowly added dropwise, and warmed to normal temperature. After the reaction was terminated, MC and 2N HCl were added, and the organic layer was extracted.

The organic layer was dried over anhydrous magnesium sulfate, suctioned, and concentrated. The resultant compound was purified by column chromatography eluting with Hex:EA=5:1, to obtain Intermediate 3 (2.48 g, 64%).

Intermediate 3 was dissolved in acetic acid, and then concentrated hydrochloric acid was added dropwise, and refluxed for 1 hr. The reaction was terminated, and extracted with diethyl ether and water. The organic layer was washed with a saturated sodium bicarbonate solution in water, dried over magnesium sulfate, recrystallized, and purified by column chromatography eluting with Hex:EA=5:1, to obtain Intermediate 4 (2.81 g, 76%).

Intermediate 3 MS(FAB): 387($M^+$)

Intermediate 4 MS(FAB): 369($M^+$)

Synthesis of Intermediate 5

[Reaction equation 3]

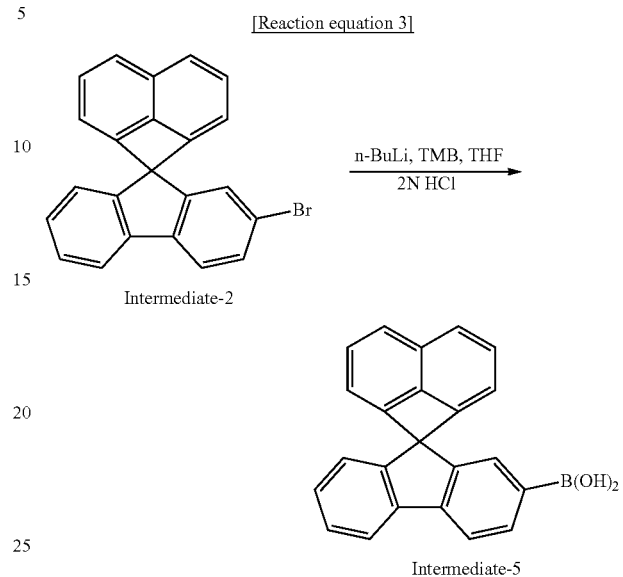

Intermediate-2

Intermediate-5

Under a nitrogen atmosphere, Intermediate 2 (3.69 g, 10 mmol) was dissolved in anhydrous tetrahydrofuran (40 mL), and cooled to −78° C. n-butyllithium (2.5 M, 4 mL) was slowly added dropwise, stirred at 0° C. for 1 hr, and then cooled to −78° C. again. Trimethyl borate (12.47 g, 12 mmol) was added dropwise, and stirred for 12 hrs at normal temperature. After the reaction was terminated, a 2N aqueous HCl solution was added, stirred for 30 min, and extracted with diethyl ether.

The organic layer was dried over anhydrous magnesium sulfate, suctioned, and concentrated. The resultant compound was purified by column chromatography eluting with Hex:EA=5:1, to obtain Intermediate 5 (2.47 g, 74%).

Intermediate 5 MS(FAB): 334(M+)

Synthesis of Intermediate 6

[Reaction equation 4]

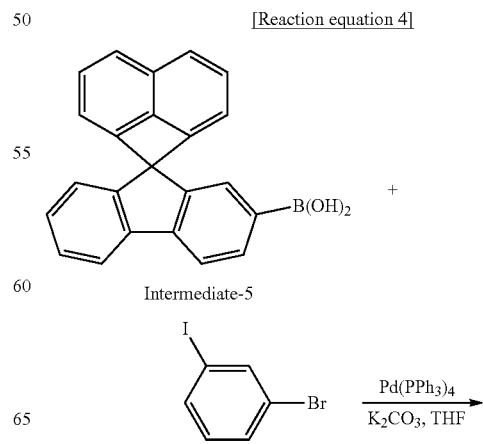

Intermediate-5

-continued

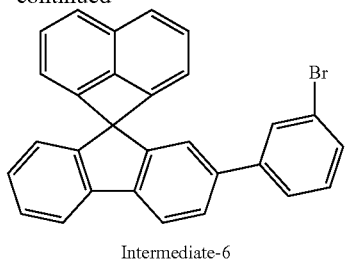

Intermediate-6

Under a nitrogen atmosphere, Intermediate 5 (3.34 g, 10 mmol) and 1-bromo-3-iodobenzene (2.83 g, 10 mmol) were mixed and dissolved in tetrahydrofuran (40 mL). Pd(PPh$_3$)$_4$ (0.58 g, 0.5 mmol) and K$_2$CO$_3$ (2 M, 30 mmol, 15 mL) were added and refluxed for 24 hrs.

After the reaction was terminated, the reactants were cooled to normal temperature, and MC (200 mL) and H$_2$O (200 mL) were added. The MC layer was extracted, dried over anhydrous magnesium sulfate, concentrated, and purified by column chromatography eluting with Hex:EA=5:1, to obtain Intermediate 6 (3.25 g, 73%).

Intermediate 6 MS(FAB): 445(M$^+$)

Synthesis of Intermediate 7

[Reaction equation 5]

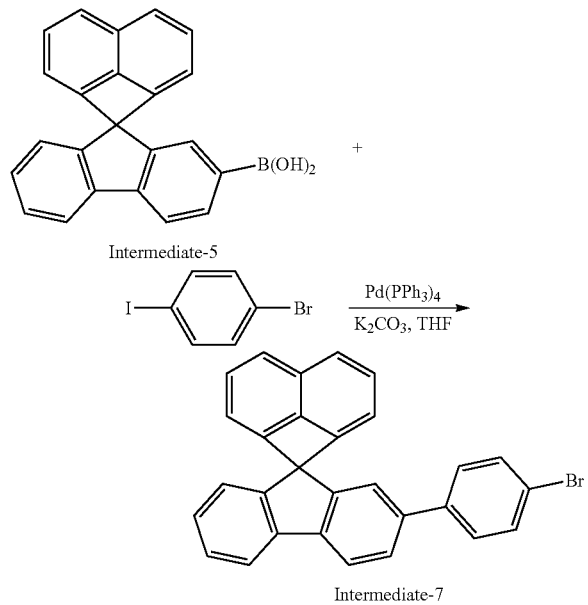

Intermediate-7

Under a nitrogen atmosphere, Intermediate 5 (3.34 g, 10 mmol) and 1-bromo-4-iodobenzene (2.83 g, 10 mmol) were mixed and dissolved in tetrahydrofuran (40 mL) Pd(PPh$_3$)$_4$ (0.58 g, 0.5 mmol) and K$_2$CO$_3$ (2 M, 15 ml, 30 mmol) were added and refluxed for 24 hrs.

After the reaction was terminated, the reactants were cooled to normal temperature, and MC (200 mL) and H$_2$O (200 mL) were added. The MC layer was extracted, dried over anhydrous magnesium sulfate, concentrated, and purified by column chromatography eluting with Hex:EA=4:1, to obtain Intermediate 7 (3.34 g, 75%).

Intermediate 7 MS(FAB): 445(M$^+$)

Synthesis of Intermediate 8 and Intermediate 9

[Reaction equation 6]

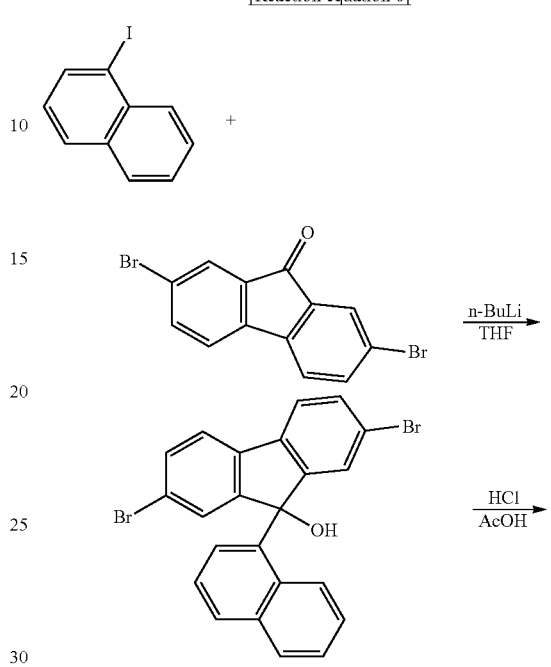

Intermediate-8

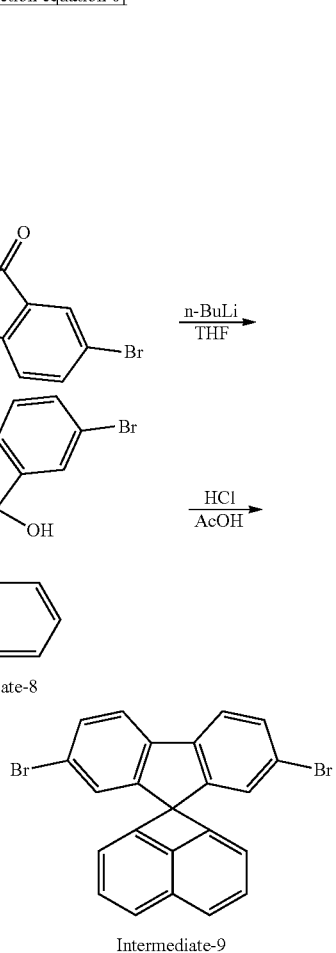

Intermediate-9

1-iodonaphthalene (2.54 g, 10 mmol) was dissolved in tetrahydrofuran (15 mL), and then cooled to −78° C. n-butyllithium (2.5 M, 4 mL) was added dropwise, and stirred at −78° C. for 1 hr. 2, 7-dibromo-9-fluorenone (3.38 g, 10 mmol) dissolved in tetrahydrofuran (30 mL) was slowly added dropwise, and warmed to normal temperature. After the reaction was terminated, MC and 2N HCl were added, and the organic layer was extracted.

The organic layer was dried over anhydrous magnesium sulfate, suctioned, and concentrated. The resultant compound was purified by column chromatography eluting with Hex:EA=3:1, to obtain Intermediate 8 (3.31 g, 71%).

Intermediate 8 was dissolved in acetic acid, and then concentrated hydrochloric acid was added dropwise, and refluxed for 1 hr. The reaction was terminated, and extracted with diethyl ether and water. The organic layer was washed with a saturated sodium bicarbonate solution in water, dried over magnesium sulfate, recrystallized, and purified by column chromatography eluting with Hex:EA=5:1, to obtain Intermediate 9 (3.45 g, 77%).

Intermediate 8 MS(FAB): 466(M$^+$)

Intermediate 9 MS(FAB): 448(M$^+$)

Synthesis of Intermediate 10

[Reaction equation 7]

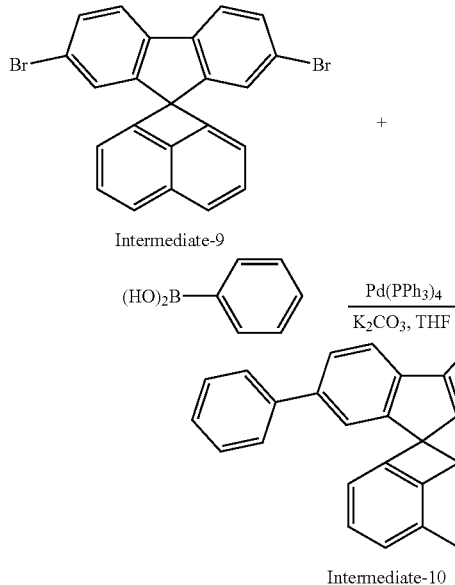

Intermediate-10

Under a nitrogen atmosphere, Intermediate 9 (4.48 g 10 mmol) and pnenymoronic acid (1.22 g, 10 mmol) were mixed and dissolved in tetrahydrofuran (40 mL) Pd(PPh$_3$)$_4$ (0.58 g, 0.5 mmol) and K$_2$CO$_3$ (2 M, 15 ml, 30 mmol) were added and refluxed for 24 hrs.

After the reaction was terminated, the reactants were cooled to normal temperature, and MC (200 mL) and H$_2$O (200 mL) were added. The MC layer was extracted, dried over anhydrous magnesium sulfate, concentrated, and purified by column chromatography eluting with Hex:EA=4:1, to obtain Intermediate 10 (3.16 g, 71%).

Intermediate 10 MS(FAB): 445(M$^+$)

Synthesis of Intermediate 11

[Reaction equation 8]

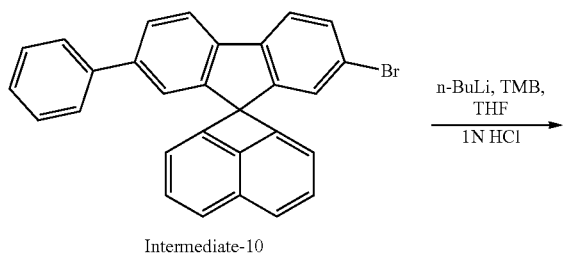

Intermediate-10

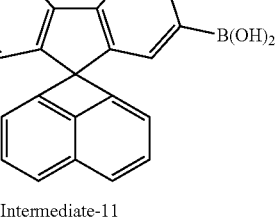

Intermediate-11

Under a nitrogen atmosphere, Intermediate 10 (4.45 g, 10 mmol) was dissolved in anhydrous tetrahydrofuran (40 mL), and then cooled to −78° C. n-butyllithium (2.5 M, 4 mL) was slowly added dropwise, stirred at 0° C. for 1 hr, and then cooled to −78° C. again. Trimethyl borate (12.47 g, 12 mmol) was added dropwise, and stirred for 12 hrs at normal temperature. After the reaction was terminated, a 2N aqueous HCl solution was added, stirred for 30 min, and extracted with diethyl ether.

The organic layer was dried over anhydrous magnesium sulfate, suctioned, and concentrated. The resultant compound was purified by column chromatography eluting with Hex:EA=4:1, to obtain Intermediate 11 (3.04 g, 74%).

Intermediate 11 MS(FAB): 410(M$^+$)

Synthesis of Intermediate 12

[Reaction equation 9]

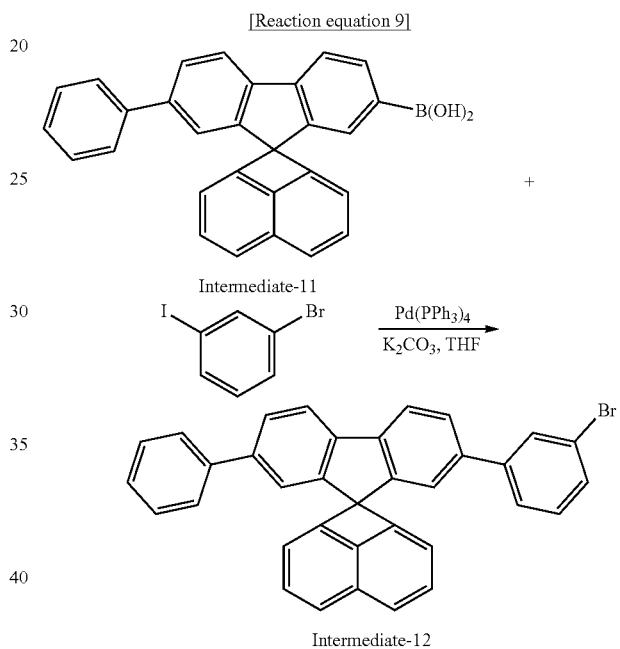

Under a nitrogen atmosphere, Intermediate 11 (4.10 g, 10 mmol) and 1-bromo-3-iodobenzene (2.83 g, 10 mmol) were mixed and dissolved in tetrahydrofuran (40 mL). Pd(PPh$_3$)$_4$ (0.58 g, 0.5 mmol) and K$_2$CO$_3$ (2 M, 30 mmol, 15 mL) were added and refluxed for 24 hrs.

After the reaction was terminated, the reactants were cooled to normal temperature, and MC (200 mL) and H$_2$O (200 mL) were added. The MC layer was extracted, dried over anhydrous magnesium sulfate, concentrated, and purified by column chromatography eluting with Hex:EA=4:1, to obtain Intermediate 12 (3.81 g, 73%).

Intermediate 12 MS(FAB): 521(M$^+$)

Synthesis of Intermediate 13

[Reaction equation 10]

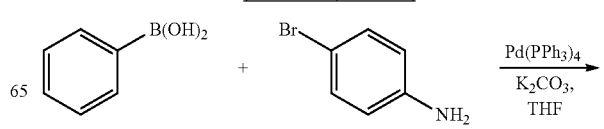

-continued

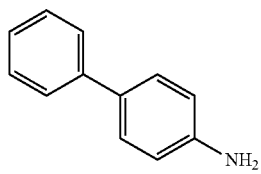

Intermediate-13

Under a nitrogen atmosphere, phenylboronic acid (1.22 g, 10 mmol) and 4-bromoaniline (1.72 g, 10 mmol) were mixed and dissolved in tetrahydrofuran (20 mL). Pd(PPh$_3$)$_4$ (0.58 g, 0.5 mmol) and K$_2$CO$_3$ (2 M, 15 ml, 30 mmol) were added and refluxed for 24 hrs.

After the reaction was terminated, the reactants were cooled to normal temperature, and MC (200 mL) and H$_2$O (200 mL) were added. The MC layer was extracted, and the organic layer was distilled under reduced pressure and purified by column chromatography eluting with Hex: MC=5:1, to obtain Intermediate 13 (1.20 g, 71%).

Intermediate 13 MS(FAB): 169(M$^+$)

Synthesis of Intermediate 14

[Reaction equation 11]

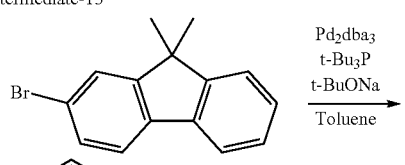

Intermediate-13

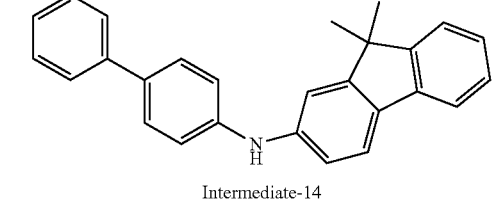

Intermediate-14

Under a nitrogen atmosphere, Intermediate 13 (1.69 g, 10 mmol) and 2-bromo-9,9-dimethyl-9H-fluorene (2.73 g, 10 mmol) were mixed and dissolved in toluene (30 mL). Pd$_2$dba$_3$ (0.18 g, 0.2 mmol), t-Bu$_3$P (1 M, 0.4 ml, 0.4 mmol), and t-BuONa (2.88 g, 30 mmol) were added and refluxed for 5 hrs.

After the reaction was terminated, the reactants were cooled to normal temperature, and toluene (200 mL) and H$_2$O (200 mL) were added. After extraction, the organic layer was dried over anhydrous magnesium sulfate to remove a small amount of water contained therein, suctioned, and concentrated. The resultant compound was purified by column chromatography eluting with Hex:MC=5:1, to obtain Intermediate 14 (2.57 g, 71%).

Intermediate 14 MS(FAB): 361(M$^+$)

Synthesis of Intermediate 15

[Reaction equation 12]

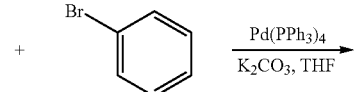

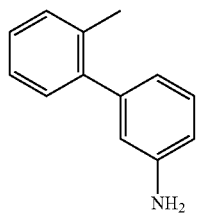

Intermediate-15

Under a nitrogen atmosphere, o-methylphenylboronic acid (1.34 g, 10 mmol) and 3-bromoaniline (1.72 g, 10 mmol) were mixed and dissolved in tetrahydrofuran (20 mL). Then Pd(PPh$_3$)$_4$ (0.58 g, 0.5 mmol) and K$_2$CO$_3$ (2 M, 15 mL, 30 mmol) were added and refluxed for 24 hrs.

After the reaction was terminated, the reactants were cooled to normal temperature, and MC (200 mL) and H$_2$O (200 mL) were added. The MC layer was extracted, and the organic layer was distilled under reduced pressure and purified by column chromatography eluting with Hex: MC=5:1, to obtain Intermediate 15 (1.25 g, 68%).

Intermediate 15 MS(FAB): 183(M$^+$)

Synthesis of Intermediate 16

[Reaction equation 13]

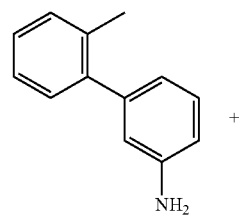

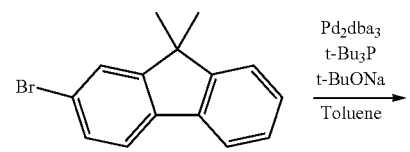

Intermediate-15

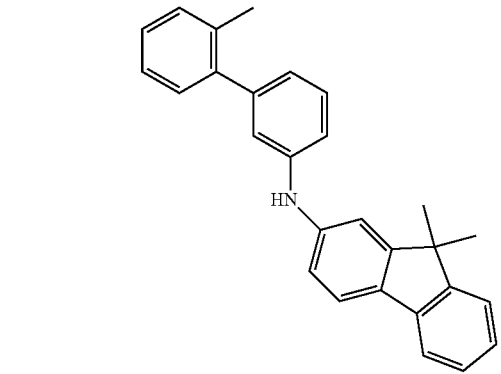

Intermediate-16

Under a nitrogen atmosphere, Intermediate 15 (1.83 g, 10 mmol) and 2-bromo-9,9-dimethyl-9H-fluorene (2.73 g, 10 mmol) were mixed and dissolved in toluene (30 mL) Pd$_2$dba$_3$ (0.18 g, 0.2 mmol), t-Bu$_3$P (1 M, 0.4 ml, 0.4 mmol), and t-BuONa (2.88 g, 30 mmol) were added and refluxed for 5 hrs.

After the reaction was terminated, the reactants were cooled to normal temperature, and toluene (200 mL) and H$_2$O (200 mL) were added. After extraction, the organic layer was dried over anhydrous magnesium sulfate to remove a small amount of water contained therein, suctioned, and concentrated. The resultant compound was purified by column chromatography eluting with Hex:MC=5:1, to obtain Intermediate 16 (2.44 g, 65%).

Intermediate 16 MS(FAB): 375(M$^+$)

Synthesis of Intermediate 17

[Reaction equation 14]

Under a nitrogen atmosphere, 2,7-dibromo-9,9-dimethyl-9H-fluorene (3.52 g, 10 mmol) and phenylboronic acid (1.22 g, 10 mmol) were mixed and dissolved in tetrahydrofuran (20 mL) Then Pd(PPh$_3$)$_4$ (0.58 g, 0.5 mmol) and K$_2$CO$_3$ (2 M, 15 mL, 30 mmol) were added and refluxed for 24 hrs.

After the reaction was terminated, MC (200 mL) and H$_2$O (200 mL) were added. The MC layer was extracted, dried over anhydrous magnesium sulfate, concentrated, and purified by column chromatography eluting with Hex:MC=5:1, to obtain Intermediate 17 (2.13 g, 61%).

Intermediate 17 MS(FAB): 349(M$^+$)

Synthesis of Intermediate 18

[Reaction equation 15]

Under a nitrogen atmosphere, Intermediate 13 (1.69 g, 10 mmol) and Intermediate 17 (3.49 g, 10 mmol) were mixed and dissolved in toluene (40 mL) Pd$_2$dba$_3$ (0.18 g, 0.2 mmol), t-Bu$_3$P (1 M, 0.4 ml, 0.4 mmol), and t-BuONa (2.88 g, 30 mmol) were added and refluxed for 5 hrs After the reaction was terminated, the reactants were cooled to normal temperature, and toluene (300 mL) and H$_2$O (300 mL) were added. After extraction, the organic layer was dried over anhydrous magnesium sulfate to remove a small amount of water contained therein, suctioned, and concentrated. The resultant compound was purified by column chromatography eluting with Hex:EA=4:1, to obtain Intermediate 18 (2.98 g, 68%).

Intermediate 18 MS(FAB): 437(M$^+$)

Synthesis of Intermediate 19

[Reaction equation 16]

-continued

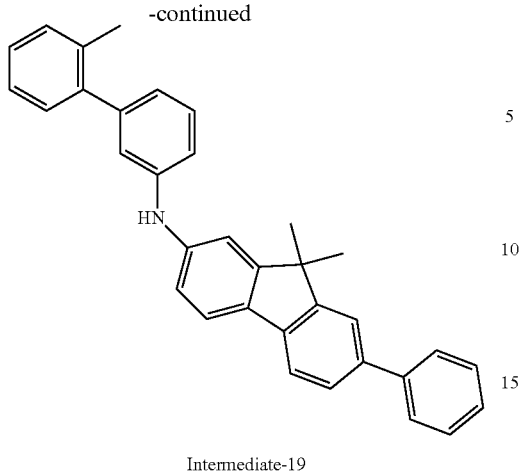

Intermediate-19

Under a nitrogen atmosphere, Intermediate 15 (1.83 g, 10 mmol) and Intermediate 17 (3.49 g, 10 mmol) were mixed and dissolved in toluene (35 mL). $Pd_2dba_3$ (0.18 g, 0.2 mmol), $t-Bu_3P$ (1 M, 0.4 ml, 0.4 mmol), and t-BuONa (2.88 g, 30 mmol) were added and refluxed for 5 hrs.

After the reaction was terminated, the reactants were cooled to normal temperature, and toluene (200 mL) and $H_2O$ (200 mL) were added. After extraction, the organic layer was dried over anhydrous magnesium sulfate to remove a small amount of water contained therein, suctioned, and concentrated. The resultant compound was purified by column chromatography eluting with Hex:EA=4:1, to obtain Intermediate 19 (2.85, g 63%).

Intermediate 19 MS(FAB): 451($M^+$)

Synthesis of Intermediate 20

[Reaction equation 17]

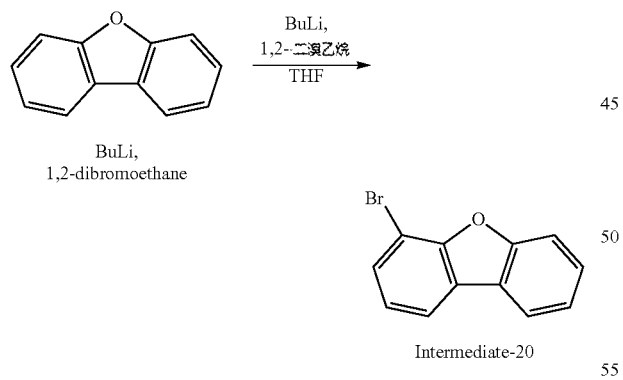

Intermediate-20

Under a nitrogen atmosphere, dibenzofuran (1.68 g, 10 mmol) was dissolved in tetrahydrofuran (10 mL), and mixed with n-BuLi (2.5 M, 4 mL) at −40° C. The cooling device was removed, and the reaction solution was placed in a water bath and warmed to room temperature in about 30 min, and then stirred for 2 hrs. Then, the reaction solution was cooled to −78° C., and 1,2-dibromoethane (2.82 g, 15 mmol) in tetrahydrofuran (10 mL) was added dropwise. The cooling device was removed, and the mixture was placed in a water bath and warmed to room temperature in about 30 min, and then stood for 2 hrs.

After the reaction was terminated, the reaction solution was washed with a saturated sodium chloride solution, taken up in a 2 N aqueous HCl solution, stirred for 30 min, and extracted with diethyl ether.

The organic layer was dried over anhydrous magnesium sulfate to remove a small amount of water contained therein, suctioned, and concentrated. The resultant compound was purified by column chromatography eluting with Hex:EA=5:1, to obtain Intermediate 20 (1.83 g, 74%).

Intermediate 20 MS(FAB): 247($M^+$)

Synthesis of Intermediate 21

[Reaction equation 18]

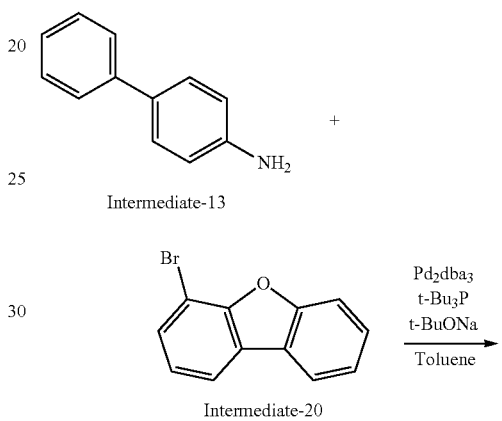

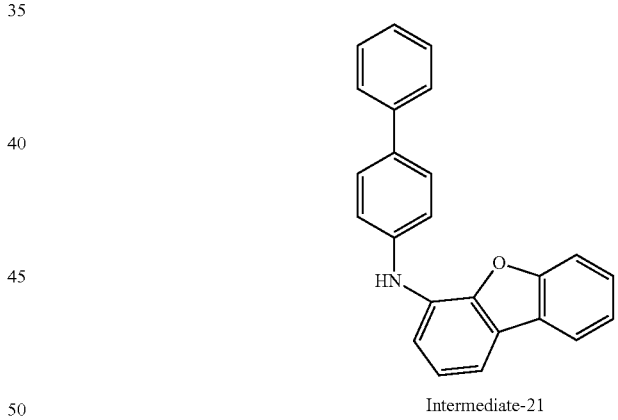

Intermediate-21

Under a nitrogen atmosphere, Intermediate 13 (1.69 g, 10 mmol) and Intermediate 20 (2.47 g, 10 mmol) were mixed and dissolved in toluene (30 mL). $Pd_2dba_3$ (0.18 g, 0.2 mmol), $t-Bu_3P$ (1 M, 0.4 ml, 0.4 mmol), and t-BuONa (2.88 g, 30 mmol) were added and refluxed for 5 hrs.

After the reaction was terminated, the reactants were cooled to normal temperature, and toluene (200 mL) and $H_2O$ (200 mL) were added. After extraction, the organic layer was dried over anhydrous magnesium sulfate to remove a small amount of water contained therein, suctioned, and concentrated. The resultant compound was purified by column chromatography eluting with Hex:EA=5:1, to obtain Intermediate 21 (2.45 g, 73%).

Intermediate 21 MS(FAB): 335($M^+$)

Synthesis of Intermediate 22

[Reaction equation 19]

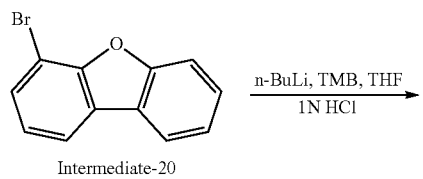

Under a nitrogen atmosphere, Intermediate 20 (2.47 g, 10 mmol) was dissolved in anhydrous tetrahydrofuran (40 mL), and then cooled to −78° C. n-butyllithium (2.5 M, 4 mL) was slowly added dropwise, stirred at 0° C. for 1 hr, and then cooled to −78° C. again. Trimethyl borate (12.47 g, 12 mmol) was added dropwise, and stirred for 12 hrs at normal temperature. After the reaction was terminated, a 2N aqueous HCl solution was added, stirred for 30 min, and extracted with diethyl ether.

The organic layer was dried over anhydrous magnesium sulfate, suctioned, and concentrated. The resultant compound was purified by column chromatography eluting with Hex:EA=5:1, to obtain Intermediate 22 (1.55 g, 73%).

Intermediate 22 MS(FAB): 212(M+)

Synthesis of Intermediate 23

[Reaction equation 20]

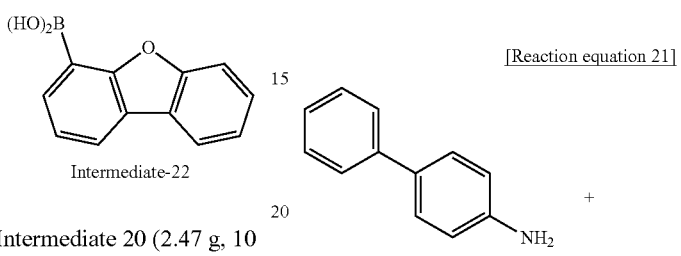

Under a nitrogen atmosphere, Intermediate 22 (2.12 g, 10 mmol) and 1-bromo-3iodobenzene (2.83 g, 10 mmol) were mixed and dissolved in tetrahydrofuran (30 mL) Pd(PPh$_3$)$_4$ (0.58 g, 0.5 mmol) and K$_2$CO$_3$ (2 M, 30 mmol, 15 mL) were added and refluxed for 24 hrs.

After the reaction was terminated, the reactants were cooled to normal temperature, and MC (200 mL) and H$_2$O (200 mL) were added. The MC layer was extracted, dried over anhydrous magnesium sulfate, concentrated, and purified by column chromatography eluting with Hex:EA=5:1, to obtain Intermediate 23 (2.23 g, 69%).

Intermediate 23 MS(FAB): 323(M+)

Synthesis of Intermediate 24

[Reaction equation 21]

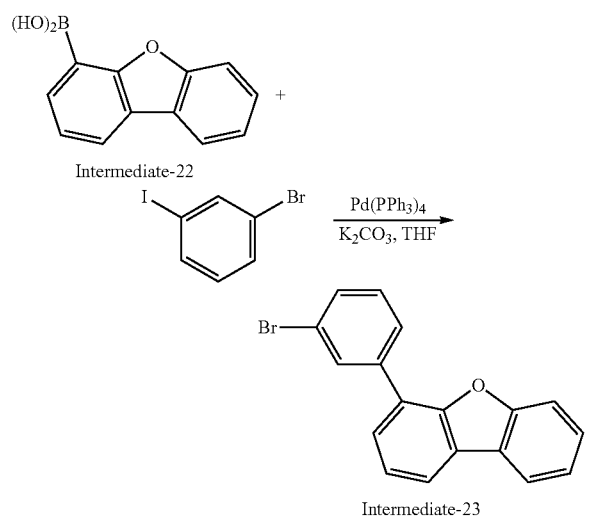

Under a nitrogen atmosphere, Intermediate 13 (1.69 g, 10 mmol) and Intermediate 23 (3.23 g, 10 mmol) were mixed and dissolved in toluene (40 mL). Pd$_2$dba$_3$ (0.18 g, 0.2 mmol), t-Bu$_3$P (1 M, 0.4 ml, 0.4 mmol), and t-BuONa (2.88 g, 30 mmol) were added and refluxed for 5 hrs.

After the reaction was terminated, the reactants were cooled to normal temperature, and toluene (200 mL) and H$_2$O (200 mL) were added. After extraction, the organic layer was dried over anhydrous magnesium sulfate to remove a small amount of water contained therein, suctioned, and concentrated. The resultant compound was purified by column chromatography eluting with Hex:EA=4:1, to obtain Intermediate 24 (3.13 g, 76%).

Intermediate 24 MS(FAB): 411(M+)

Synthesis of Intermediate 25

[Reaction equation 22]

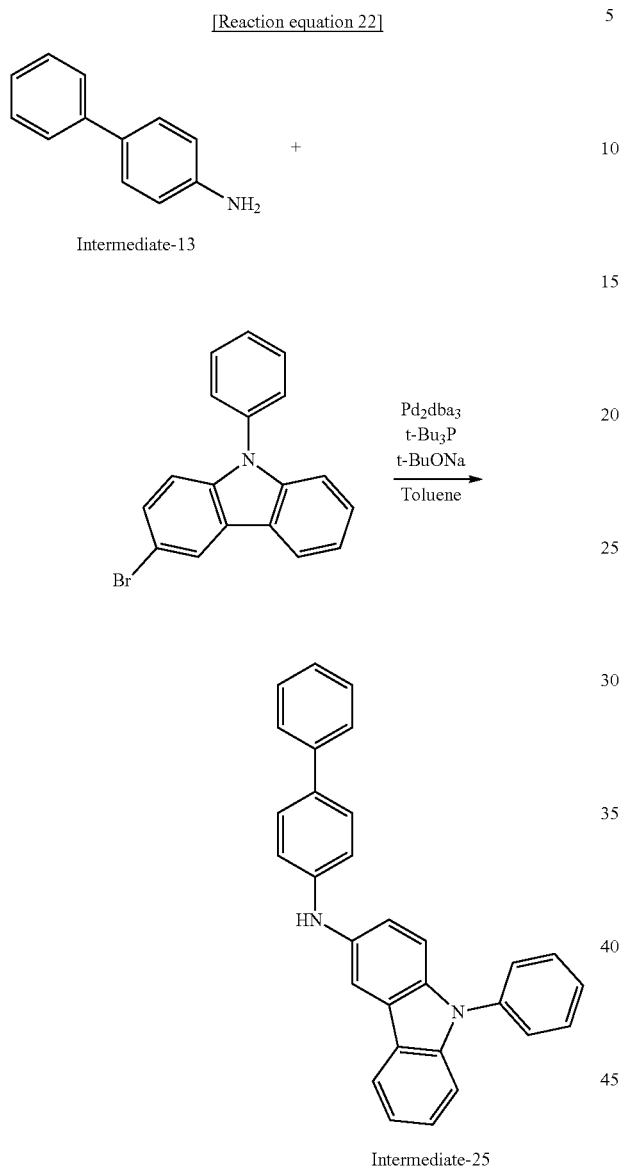

Intermediate-25

Under a nitrogen atmosphere, Intermediate 13 (1.69 g, 10 mmol) and 3-bromo-9-phenyl-9H-carbazolyl (3.22 g, 10 mmol) were mixed and dissolved in toluene (40 mL) Pd$_2$dba$_3$ (0.18 g, 0.2 mmol), t-Bu$_3$P (1 M, 0.4 ml, 0.4 mmol), and t-BuONa (2.88 g, 30 mmol) were added and refluxed for 5 hrs.

After the reaction was terminated, the reactants were cooled to normal temperature, and toluene (200 mL) and H$_2$O (200 mL) were added. After extraction, the organic layer was dried over anhydrous magnesium sulfate to remove a small amount of water contained therein, suctioned, and concentrated. The resultant compound was purified by column chromatography eluting with Hex:EA=4:1, to obtain Intermediate 25 (3.20 g, 78%).

Intermediate 25 MS(FAB): 410(M$^+$)

Synthesis of Intermediate 26

[Reaction equation 23]

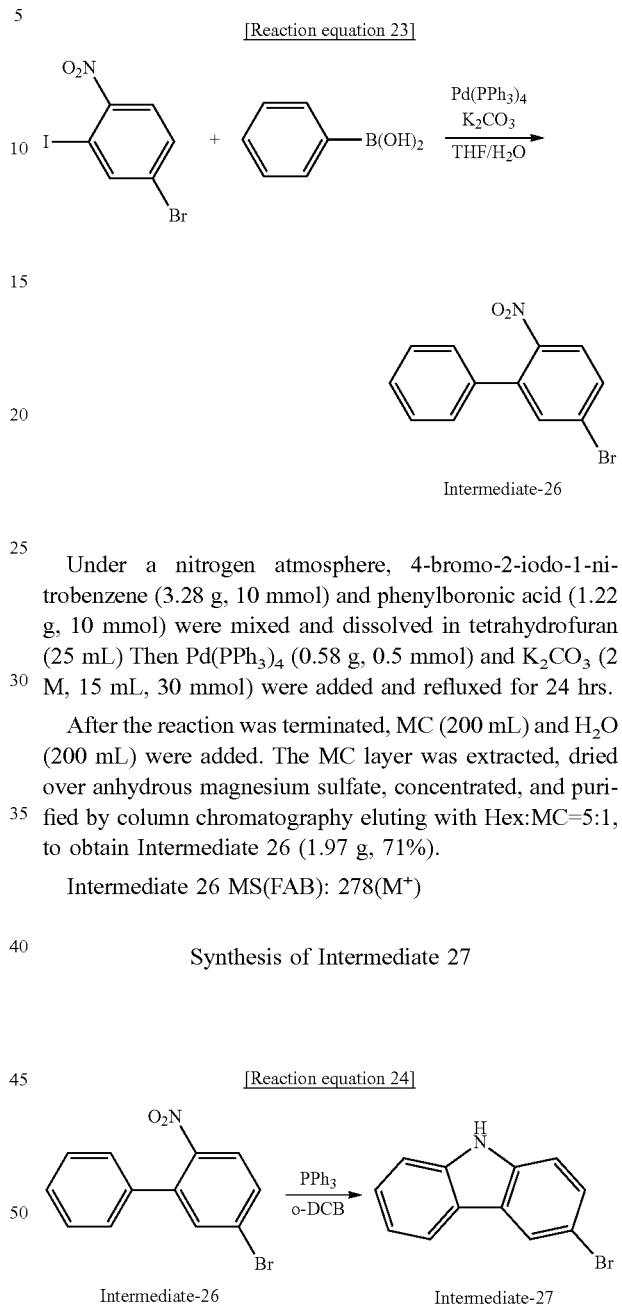

Under a nitrogen atmosphere, 4-bromo-2-iodo-1-nitrobenzene (3.28 g, 10 mmol) and phenylboronic acid (1.22 g, 10 mmol) were mixed and dissolved in tetrahydrofuran (25 mL) Then Pd(PPh$_3$)$_4$ (0.58 g, 0.5 mmol) and K$_2$CO$_3$ (2 M, 15 mL, 30 mmol) were added and refluxed for 24 hrs.

After the reaction was terminated, MC (200 mL) and H$_2$O (200 mL) were added. The MC layer was extracted, dried over anhydrous magnesium sulfate, concentrated, and purified by column chromatography eluting with Hex:MC=5:1, to obtain Intermediate 26 (1.97 g, 71%).

Intermediate 26 MS(FAB): 278(M$^+$)

Synthesis of Intermediate 27

[Reaction equation 24]

Under a nitrogen atmosphere, Intermediate 26 (2.78 g, 10 mmol) was dissolved in o-DCB (40 mL), and then triphenylphosphine (6.56 g, 25 mmol) was added dropwise and refluxed.

After the reaction was terminated, MC (200 mL) and H$_2$O (200 mL) were added. The MC layer was extracted, dried over anhydrous magnesium sulfate, concentrated, and purified by column chromatography eluting with Hex:MC=5:1, to obtain Intermediate 27 (1.94 g, 79%).

Intermediate 27 MS(FAB): 246(M$^+$)

Synthesis of Intermediate 28

[Reaction equation 25]

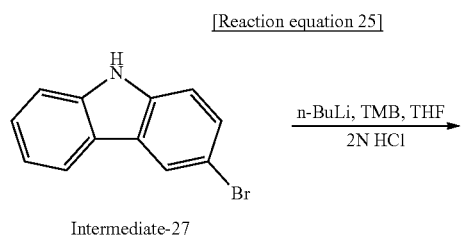

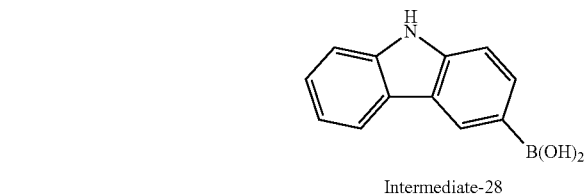

Under a nitrogen atmosphere, Intermediate 27 (2.46 g, 10 mmol) was dissolved in anhydrous tetrahydrofuran (40 mL), and then cooled to −78° C. n-butyllithium (2.5 M, 4 mL) was slowly added dropwise, stirred at 0° C. for 1 hr, and then cooled to −78° C. again. Trimethyl borate (12.47 g, 12 mmol) was added dropwise, and stirred for 12 hrs at normal temperature. After the reaction was terminated, a 2N aqueous HCl solution was added, stirred for 30 min, and extracted with diethyl ether.

The organic layer was dried over anhydrous magnesium sulfate, suctioned, and concentrated. The resultant compound was purified by column chromatography eluting with Hex:EA=5:1, to obtain Intermediate 28 (1.56 g, 74%).

Intermediate 28 MS(FAB): 211(M+)

Synthesis of Intermediate 29

[Reaction equation 26]

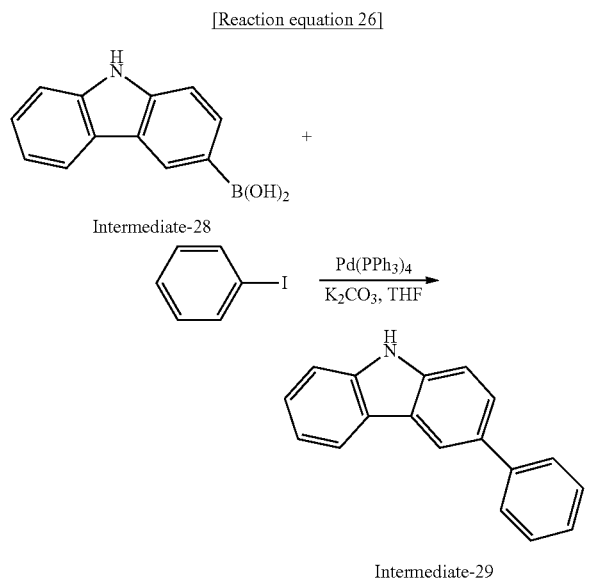

Under a nitrogen atmosphere, Intermediate 28 (2.11 g, 10 mmol) and iodobenzene (2.04 g, 10 mmol) were mixed and dissolved in tetrahydrofuran (30 mL). Pd(PPh$_3$)$_4$ (0.58 g, 0.5 mmol) and K$_2$CO$_3$ (2 M, 30 mmol, 15 mL) were added and refluxed for 24 hrs.

After the reaction was terminated, the reactants were cooled to normal temperature, and MC (200 mL) and H$_2$O (200 mL) were added. The MC layer was extracted, dried over anhydrous magnesium sulfate, concentrated, and purified by column chromatography eluting with Hex:EA=5:1, to obtain Intermediate 29 (1.73 g, 71%).

Intermediate 29 MS(FAB): 243(M+)

Synthesis of Intermediate 30

[Reaction equation 27]

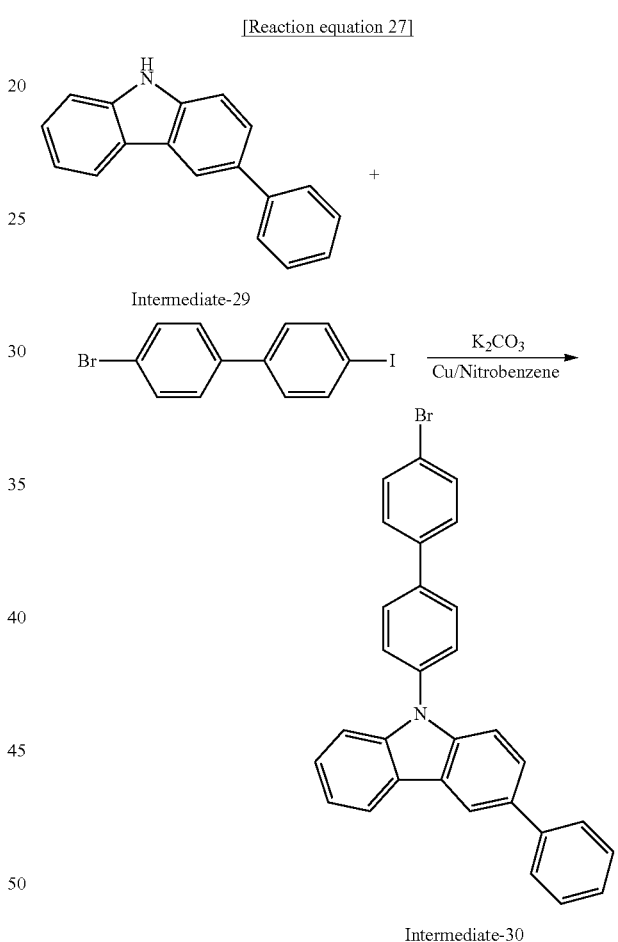

Under a nitrogen atmosphere, Intermediate 29 (2.43 g, 10 mmol) and 4-bromo-4'-iodo-1,1'-biphenyl (5.39 g, 15 mmol) were dissolved in nitrobenzene (50 mL). K$_2$CO$_3$ (4.15 g, 30 mmol) and Cu (0.19 g, 3 mmol) were added and refluxed for 16 hrs.

After the reaction was terminated, nitrobenzene was removed by distillation, and MC (200 mL) and H$_2$O (200 mL) were added. The MC layer was extracted, dried over anhydrous magnesium sulfate, concentrated, and purified by column chromatography eluting with Hex:EA=3:1, to obtain Intermediate 30 (3.65 g, 77%).

Intermediate 30 MS(FAB): 474(M)

Synthesis of Intermediate 31

[Reaction equation 28]

Intermediate-13 + Intermediate-30 → Intermediate-31

Pd$_2$dba$_3$, t-Bu$_3$P, t-BuONa, Toluene

Under a nitrogen atmosphere, Intermediate 13 (1.69 g, 10 mmol) and Intermediate 30 (4.74 g, 10 mmol) were mixed and dissolved in toluene (50 mL) Pd$_2$dba$_3$ (0.18 g, 0.2 mmol), t-Bu$_3$P (1 M, 0.4 ml, 0.4 mmol), and t-BuONa (2.88 g, 30 mmol) were added and refluxed for 7 hrs.

After the reaction was terminated, the reactants were cooled to normal temperature, and toluene (300 mL) and H$_2$O (300 mL) were added. After extraction, the organic layer was dried over anhydrous magnesium sulfate to remove a small amount of water contained therein, suctioned, and concentrated. The resultant compound was purified by column chromatography eluting with Hex:EA=3:1, to obtain Intermediate 31 (4.05 g, 72%).

Intermediate 31 MS(FAB): 562(M$^+$)

Synthesis of Compound [2]

[Reaction equation 29]

Intermediate-2 + Intermediate-14 → Compound 2

Pd$_2$dba$_3$, t-Bu$_3$P, t-BuONa, Toluene

Under a nitrogen atmosphere, Intermediate 2 (3.69 g, 10 mmol) and Intermediate 14 (3.61 g, 10 mmol) were mixed and dissolved in toluene (50 mL). Pd$_2$dba$_3$ (0.18 g, 0.2 mmol), t-Bu$_3$P (0.4 ml, 0.4 mmol), and t-BuONa (2.88 g, 30 mmol) were added and refluxed for 12 hrs.

After the reaction was terminated, MC (300 mL) and H$_2$O (300 mL) were added. The MC layer was extracted, and the organic layer was suctioned and purified by column chromatography eluting with Hex:MC=3:1, to obtain Compound 2 (5.39 g, 83%).

1H NMR (DMSO, 300 Hz): δ (ppm)=8.20-8.10 (m, 2H), 8.10-7.80 (m, 2H), 7.75-6.90 (m, 21H), 6.90-6.55 (m, 4H), 1.35 (s, 6H) MS(FAB): 649(M)

Synthesis of Compound [5]

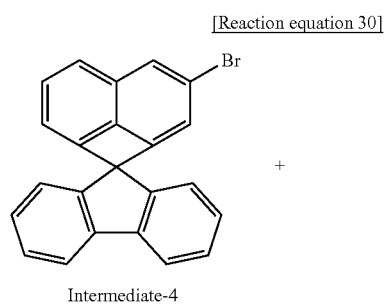

Intermediate-4

+

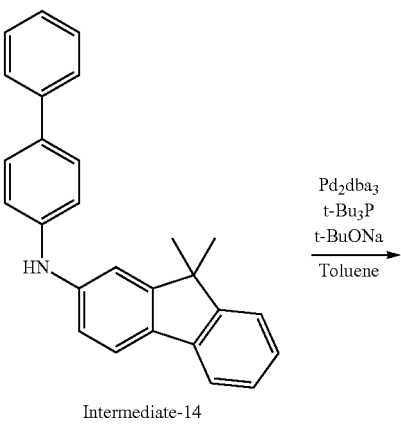

Intermediate-14

$\xrightarrow[\text{Toluene}]{\substack{\text{Pd}_2\text{dba}_3 \\ \text{t-Bu}_3\text{P} \\ \text{t-BuONa}}}$

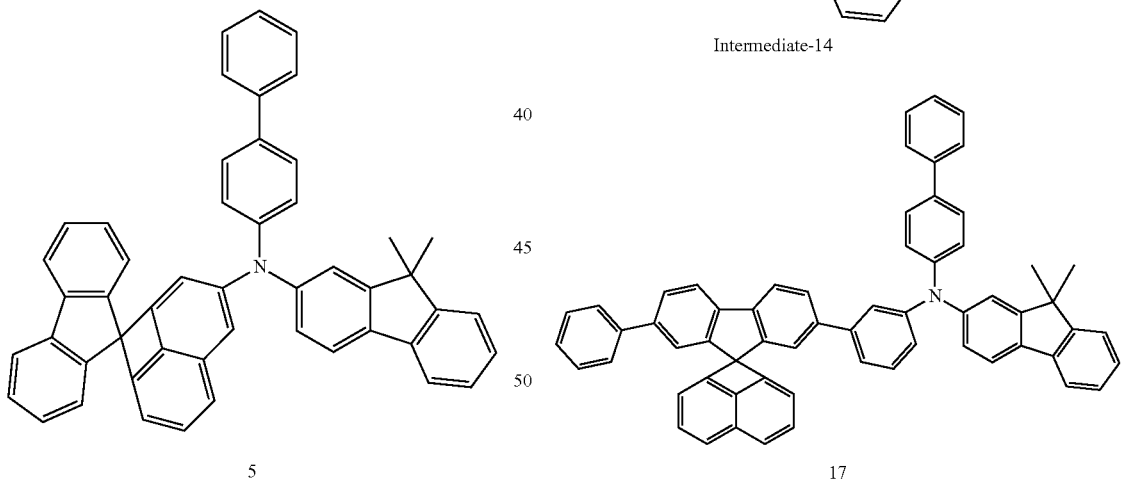

Under a nitrogen atmosphere, Intermediate 4 (3.69 g, 10 mmol) and Intermediate 14 (3.61 g, 10 mmol) were mixed and dissolved in toluene (50 mL). Pd$_2$dba$_3$ (0.18 g, 0.2 mmol), t-Bu$_3$P (0.4 ml, 0.4 mmol), and t-BuONa (2.88 g, 30 mmol) were added and refluxed for 12 hrs.

After the reaction was terminated, MC (300 mL) and H$_2$O (300 mL) were added. The MC layer was extracted, and the organic layer was suctioned and purified by column chromatography eluting with Hex:MC=3:1, to obtain Compound 5 (4.94 g, 76%).

1H NMR (DMSO, 300 Hz): δ (ppm)=8.20-8.07 (m, 2H), 8.07-7.75 (m, 2H), 7.75-6.90 (m, 21H), 6.90-6.55 (m, 4H), 1.35 (s, 6H) MS(FAB): 649(M$^+$)

Synthesis of Compound [17]

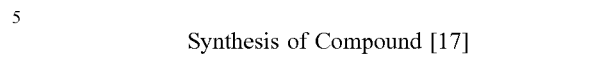

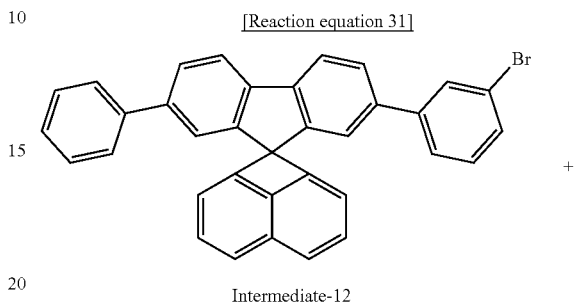

Intermediate-12

+

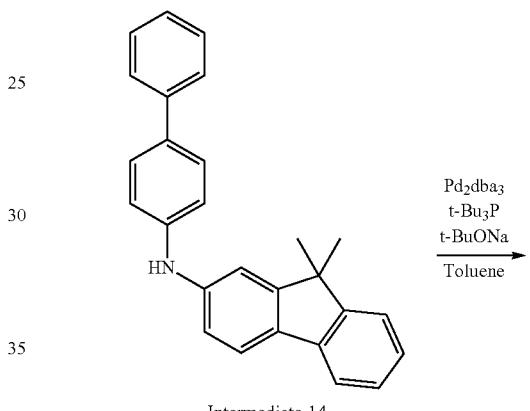

Intermediate-14

$\xrightarrow[\text{Toluene}]{\substack{\text{Pd}_2\text{dba}_3 \\ \text{t-Bu}_3\text{P} \\ \text{t-BuONa}}}$ Under a nitrogen atmosphere, Intermediate 12 (5.21 g, 10 mmol) and Intermediate 14 (3.61 g, 10 mmol) were mixed and dissolved in toluene (50 mL). Pd$_2$dba$_3$ (0.18 g, 0.2 mmol), t-Bu$_3$P (0.4 ml, 0.4 mmol), and t-BuONa (2.88 g, 30 mmol) were added and refluxed for 12 hrs.

After the reaction was terminated, MC (400 mL) and H$_2$O (400 mL) were added. The MC layer was extracted, and the organic layer was suctioned and purified by column chromatography eluting with Hex:MC=2:1, to obtain Compound 17 (6.26 g, 78%).

1H NMR (DMSO, 300 Hz): δ (ppm)=8.23-8.09 (m, 2H), 8.09-7.78 (m, 2H), 7.73-6.88 (m, 29H), 6.88-6.55 (m, 4H), 1.35 (s, 6H) MS(FAB): 802(M+)

Synthesis of Compound [20]

[Reaction equation 32]

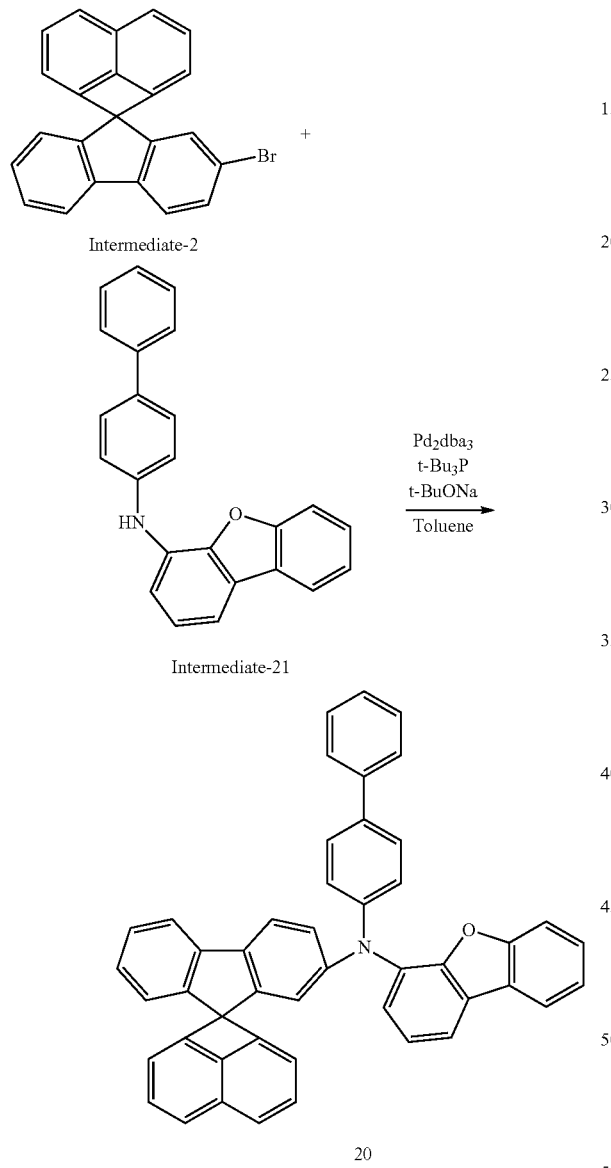

Under a nitrogen atmosphere, Intermediate 2 (3.69 g, 10 mmol) and Intermediate 21 (3.35 g, 10 mmol) were mixed and dissolved in toluene (40 mL). Pd$_2$dba$_3$ (0.18 g, 0.2 mmol), t-Bu$_3$P (0.4 ml, 0.4 mmol), and t-BuONa (2.88 g, 30 mmol) were added and refluxed for 12 hrs.

After the reaction was terminated, MC (300 mL) and H$_2$O (300 mL) were added. The MC layer was extracted, and the organic layer was suctioned and purified by column chromatography eluting with Hex:MC=3:1, to obtain Compound 20 (5.05 g, 81%).

1H NMR (DMSO, 300 Hz): δ (ppm)=8.20-8.07 (m, 2H), 8.07-7.85 (m, 3H), 7.85-6.90 (m, 20H), 6.90-6.55 (m, 4H) MS(FAB): 623(M+)

Synthesis of Compound [28]

[Reaction equation 33]

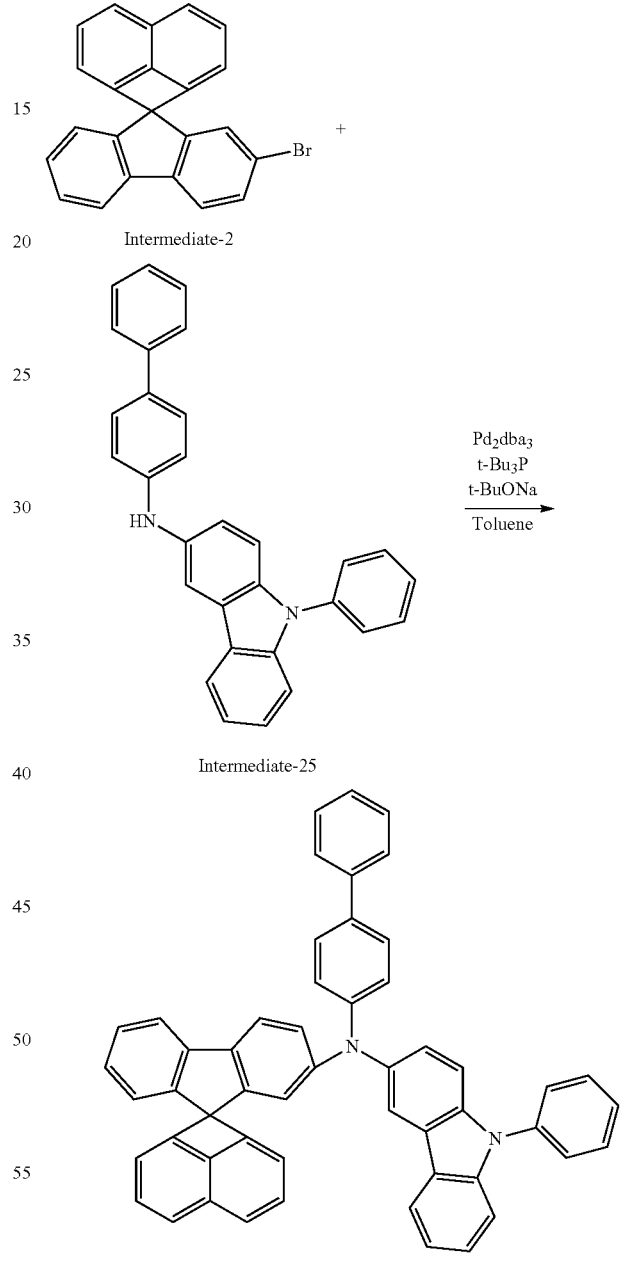

Under a nitrogen atmosphere, Intermediate 2 (3.69 g, 10 mmol) and Intermediate 25 (4.11 g, 10 mmol) were mixed and dissolved in toluene (60 mL) Pd$_2$dba$_3$ (0.18 g, 0.2 mmol), t-Bu$_3$P (0.4 ml, 0.4 mmol), and t-BuONa (2.88 g, 30 mmol) were added and refluxed for 12 hrs.

After the reaction was terminated, MC (300 mL) and H₂O (300 mL) were added. The MC layer was extracted, and the organic layer was suctioned and purified by column chromatography eluting with Hex:MC=3:1, to obtain Compound 28 (5.66 g, 81%).

1H NMR (DMSO, 300 Hz): δ (ppm)=8.40-8.05 (m, 5H), 8.05-7.80 (m, 1H), 7.80-6.90 (m, 24H), 6.90-6.55 (m, 4H) MS(FAB): 698(M⁺)

Synthesis of Compound [41]

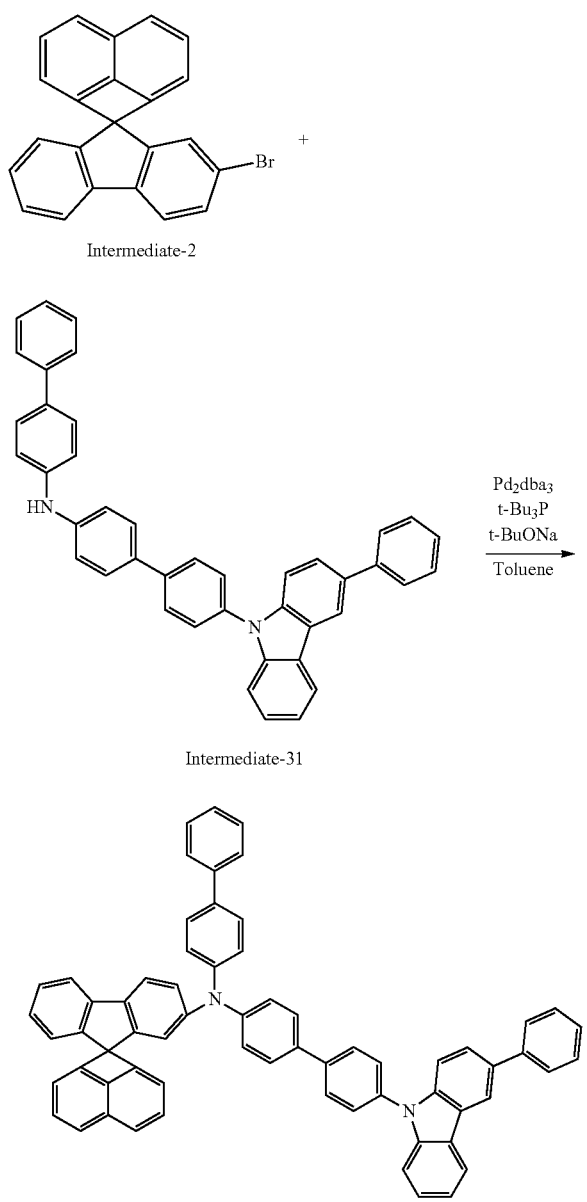

[Reaction equation 34]

Intermediate-2

Intermediate-31

41

Under a nitrogen atmosphere, Intermediate 2 (3.69 g, 10 mmol) and Intermediate 31 (5.63 g, 10 mmol) were mixed and dissolved in toluene (70 mL). Pd₂dba₃ (0.18 g, 0.2 mmol), t-Bu₃P (0.4 ml, 0.4 mmol), and t-BuONa (2.88 g, 30 mmol) were added and refluxed for 12 hrs.

After the reaction was terminated, MC (400 mL) and H₂O (400 mL) were added. The MC layer was extracted, and the organic layer was suctioned and purified by column chromatography eluting with Hex:MC=2:1, to obtain Compound 41 (6.64 g, 78%).

1H NMR (DMSO, 300 Hz): δ (ppm)=8.40-8.05 (m, 5H), 8.05-7.85 (m, 1H), 7.85-6.90 (m, 32H), 6.90-6.55 (m, 4H) MS(FAB): 851(M⁺)

Compounds 1 to 49 of General Formula 1 can be prepared following the processes described in Reaction equations 1-34.

Hereinafter, the present invention is described in further detail with reference to examples. However, the examples are merely illustrative of the present invention specifically, and the protection scope of the present invention is not limited thereto. Appropriate modifications and changes may be made to the examples by those skilled in the art without departing from the protection scope of the present invention.

Examples 1-15: Fabrication of Organic Electroluminescence Devices

An ITO anode (5 Ω/cm², 1200 Å) coated glass substrate was cut to have a size of 45 mm×45 mm×0.7 mm, ultrasonicated for 5 min in isopropanol and pure water, rinsed for 30 min with ozone under UV irradiation, and then disposed on a vacuum coating equipment.

On the top of the ITO coating, 2-TNATA was deposited to form a hole injection layer of 300 Å in thickness; and a corresponding ingredient was selected from Compounds 2, 5, 6, 7, 12, 17, 20, 25, 28, 33, 34, 38, 41, 45, and 49 of the present invention and deposited under vacuum on a surface of the hole injection layer, to form a hole transport layer of 900 Å in thickness.

Then, AND and DPAVBi were deposited at a weight ratio of 97:3 under vacuum on a surface of the hole transport layer, to form an emission layer of 300 Å in thickness.

Then, Alq₃ was deposited on a surface of the emission layer, to form an electron transport layer of 300 Å in thickness; LiF was deposited on a surface of the electron transport layer, to form an electron injection layer of 10 Å in thickness; Al was deposited on a surface of the electron injection layer, to form a second electrode (cathode) of 1000 Å in thickness. In this way, an organic electroluminescence device was obtained. The organic electroluminescence device was sealed with a water absorbing material containing a UV curable binder on a surface of the cathode, to protect the organic electroluminescence device from being influenced by oxygen or moisture in the atmosphere.

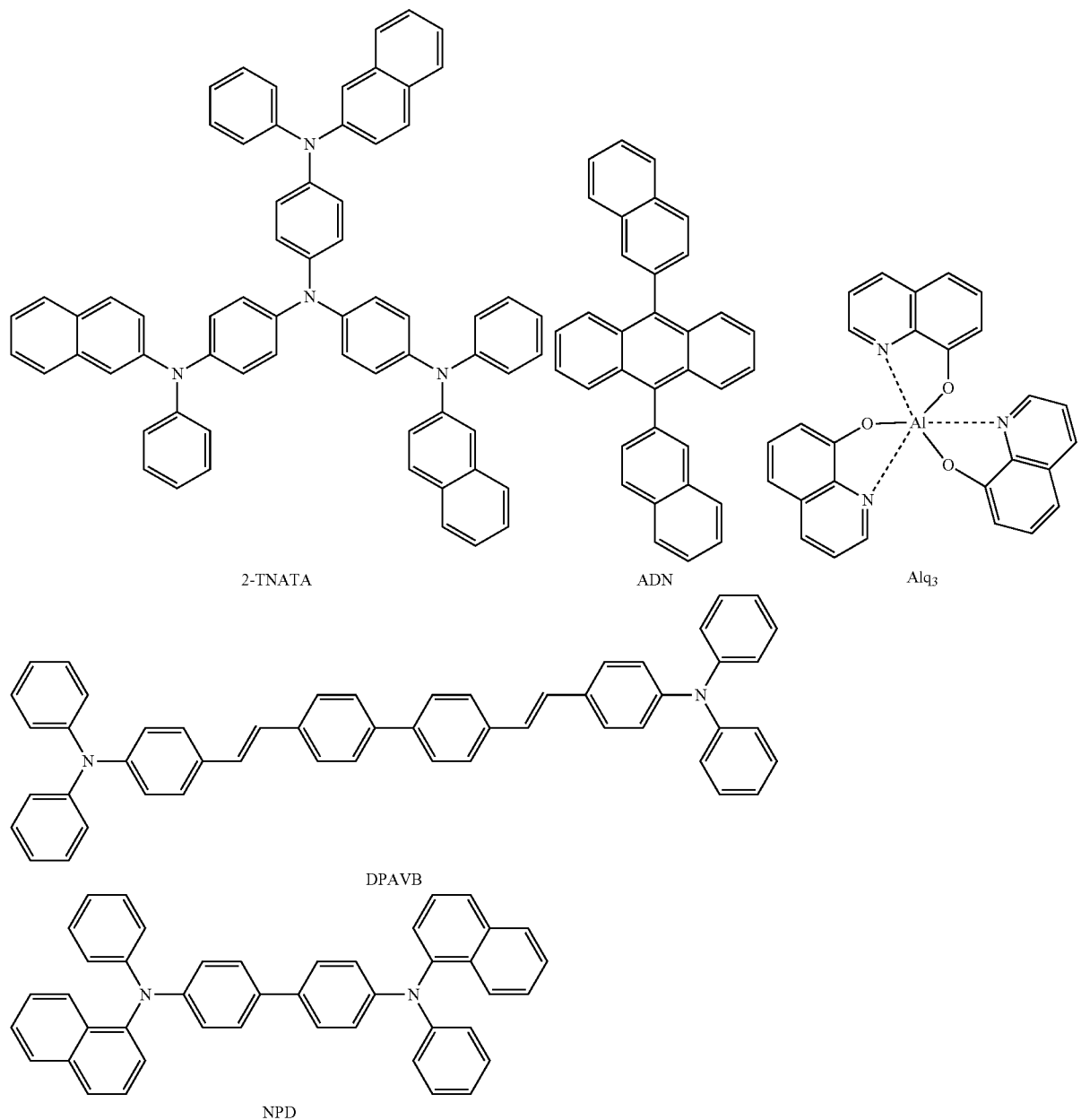

Comparative Example 1: Fabrication of Organic Electroluminescence Device

This example was the same as Example 1 except that α-NPD was used as the electron transport layer in place of the compound of the present invention.

Experiment Example 1: Characteristic Evaluation of Organic Electroluminescence Devices The characteristics of the organic electroluminescence devices 1 to 15 fabricated in the examples and the organic electroluminescence device fabricated in the comparative example were determined at a current density of 10 mA/cm$^2$. The results are shown in Table 1.

TABLE 1

| | Material | Current density (mA/cm$^2$) | Voltage (V) | Luminous efficiency (Cd/A) | CIE system (X Y) |
|---|---|---|---|---|---|
| Comparative Example 1 | NPD | 10 | 4.1 | 4.50 | (0.150 0.090) |
| Example1 | Compound 2 | 10 | 4.0 | 7.27 | (0.149 0.088) |
| Example2 | Compound 5 | 10 | 4.1 | 7.43 | (0.150 0.089) |
| Example3 | Compound 6 | 10 | 4.0 | 6.96 | (0.150 0.086) |
| Example4 | Compound 7 | 10 | 3.9 | 7.62 | (0.151 0.090) |
| Example5 | Compound 12 | 10 | 3.9 | 7.63 | (0.150 0.089) |

TABLE 1-continued

| Material | | Current density (mA/cm$^2$) | Voltage (V) | Luminous efficiency (Cd/A) | CIE system (X Y) |
|---|---|---|---|---|---|
| Example6 | Compound 17 | 10 | 4.0 | 7.69 | (0.150 0.090) |
| Example7 | Compound 20 | 10 | 3.9 | 7.41 | (0.148 0.089) |
| Example8 | Compound 25 | 10 | 3.9 | 7.49 | (0.150 0.088) |
| Example9 | Compound 28 | 10 | 4.0 | 7.48 | (0.149 0.089) |
| Example10 | Compound 33 | 10 | 3.9 | 7.51 | (0.150 0.089) |
| Example11 | Compound 34 | 10 | 3.7 | 7.33 | (0.149 0.089) |
| Example12 | Compound 38 | 10 | 3.8 | 7.59 | (0.150 0.087) |
| Example13 | Compound 41 | 10 | 4.1 | 7.83 | (0.150 0.091) |
| Example14 | Compound 45 | 10 | 4.0 | 7.38 | (0.150 0.087) |
| Example15 | Compound 49 | 10 | 4.0 | 7.45 | (0.150 0.090) |

It can be seen from the experimental results in Table 1 that the organic electroluminescence devices fabricated in Example 1 to 15 of the present invention have obviously increased luminous efficiency, compared with the existing electroluminescence device fabricated in Comparative Example 1.

Further, it can be known from the experimental results above that for the examples where the organic compound of the present invention is used as a hole transport substance, the luminous efficiency of the organic electroluminescence devices is improved. Therefore, the organic compound of the present invention enables the device to be driven at a reduced voltage, and can reduce the power consumption as well. Furthermore, the luminous service of the organic electroluminescence devices is also enhanced.

What is claimed is:

1. An organic compound of General Formula 1:

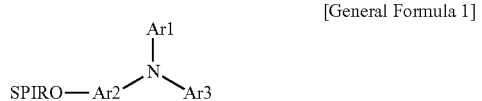

[General Formula 1]

wherein in General Formula (1), SPIRO is a unit represented by General Formula (2) below:

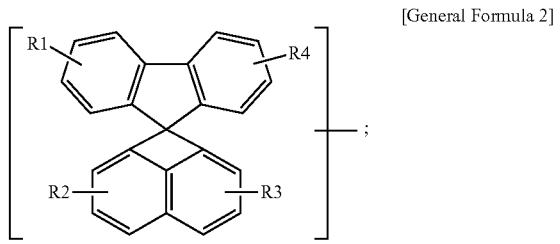

[General Formula 2]

Ar1 and Ar3 are the same or different, and are selected from the group consisting of benzene optionally substituted with one or more radicals R5, biphenyl optionally substituted with one or more radicals R5, naphthalene optionally substituted with one or more radicals R5, phenanthrene optionally substituted with one or more radicals R5, fluorene optionally substituted with one or more radicals R5, dibenzofuran optionally substituted with one or more radicals R5, dibenzothiophene optionally substituted with one or more radicals R5, substituted or unsubstituted spirobifluorene, and a combination of 2, 3, 4, or 5 of these groups;

Ar2 is absent or selected from the group consisting of benzene optionally substituted with one or more radicals R5, biphenyl optionally substituted with one or more radicals R5, naphthalene optionally substituted with one or more radicals R5, phenanthrene optionally substituted with one or more radicals R5, fluorene optionally substituted with one or more radicals R5, spirobifluorene optionally substituted with one or more radicals R5, dibenzofuran optionally substituted with one or more radicals R5, and dibenzothiophene optionally substituted with one or more radicals R5;

R5 is selected from the group consisting of (i) H, D, F, Cl, Br, I, CN, Si(R2)$_3$, (ii) a linear alkyl, alkoxy or thioalkyl having 1 to 31 carbon atoms, (iii) a branched alkyl, cycloalkyl, branch alkoxy, or branched thioalkyl having 3 to 31 carbon atoms, (iv) benzene, naphthalene, phenanthrene, fluorene, spirobifluorene, dibenzofuran, dibenzothiophene, and a combination of 2, 3, 4, or 5 of these groups, (v) an aryloxy having 5 to 40 aromatic ring atoms, and (vi) an aralkyl having 5 to 40 aromatic ring atoms, wherein when there are a plurality of R5's in General Formula (1), R5's are the same or different;

R2 is selected from the group consisting of (i) H, D, F, Cl, Br, I, CN, (ii) a linear alkyl, alkoxy or thioalkyl having 1 to 40 carbon atoms, (iii) a branched alkyl, cycloalkyl, branched alkoxy, or branched thioalkyl having 3 to 40 carbon atoms, (iv) benzene, naphthalene, phenanthrene, fluorene, spirobifluorene, dibenzofuran, dibenzothiophene, and a combination of 2, 3, 4, or 5 of these groups, (v) an aryloxy having 5 to 60 aromatic ring atoms, and (vi) an aralkyl having 5 to 60 aromatic ring atoms; and R1, R3, and R4 are the same or different, and are selected from the group consisting of (i) H, D, F, Cl, Br, I, CN, Si(R2)$_3$, (ii) a linear alkyl, alkoxy or thioalkyl having 1 to 40 carbon atoms (iii) a branched alkyl, cycloalkyl, branched alkoxy, or branched thioalkyl having 3 to 40 carbon atoms, (iv) benzene, naphthalene, phenanthrene, fluorene, spirobifluorene, dibenzofuran, dibenzothiophene, and a combination of 2, 3, 4, or 5 of these groups, (v) an aryloxy having 5 to 60 aromatic ring atoms, and (vi) an aralkyl having 5 to 60 aromatic ring atoms.

2. The organic compound according to claim 1, wherein:

Ar1 and Ar3 are the same or different in each case and elected from the group consisting of benzene optionally substituted with one or more radicals R5, naphthalene optionally substituted with one or more radicals R5, phenanthrene optionally substituted with one or more radicals R5, fluorene optionally substituted with one or more radicals R5, dibenzofuran optionally substituted with one or more radicals R5, dibenzothiophene optionally substituted with one or more radicals R5, and substituted or unsubstituted spirobifluorene;

Ar2 is absent or selected from the group consisting of benzene optionally substituted with one or more radicals R5, naphthalene optionally substituted with one or more radicals R5, phenanthrene optionally substituted with one or more radicals R5, fluorene optionally substituted with one or more radicals R5, spirobifluorene optionally substituted with one or more radicals R5, dibenzofuran optionally substituted with one or more radicals R5, and dibenzothiophene optionally substituted with one or more radicals R5;

R2 is selected from the group consisting of (i) H, D, F, Cl, Br, I, CN, (ii) a linear alkyl, alkoxy or thioalkyl having 1 to 25 carbon atoms, (iii) a branched alkyl, cycloalkyl, branched alkoxy, or branched thioalkyl having 3 to 25 carbon atoms, (iv) benzene, naphthalene, phenanthrene, fluorene, spirobifluorene, dibenzofuran, and dibenzothiophene, (v) an aryloxy having 5 to 31 aromatic ring atoms, and (vi) an aralkyl having 5 to 31 aromatic ring atoms; and R1, R3, R4, and R5 are the same or different and are selected from the group consisting of (i) H, D, F, Cl, Br, I, CN, Si(R2)$_3$, (ii) a linear alkyl, alkoxy or thioalkyl having 1 to 25 carbon atoms, (iii) a branched alkyl, cycloalkyl, branched alkoxy, or branched thioalkyl having 3 to 5 carbon atoms, (iv) benzene, naphthalene, phenanthrene, fluorene, spirobifluorene, dibenzofuran, and dibenzothiophene, (v) an aryloxy having 5 to 31 aromatic ring atoms, and (vi) an aralkyl having 5 to 31 aromatic ring atoms.

3. The organic compound according to claim 1, wherein:

the organic compound is any one of Compounds 1 to 49 below:

1

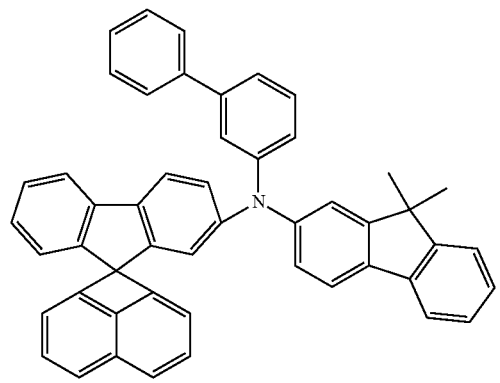

2

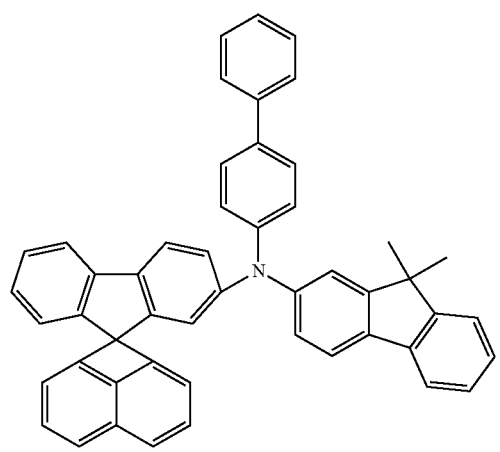

3

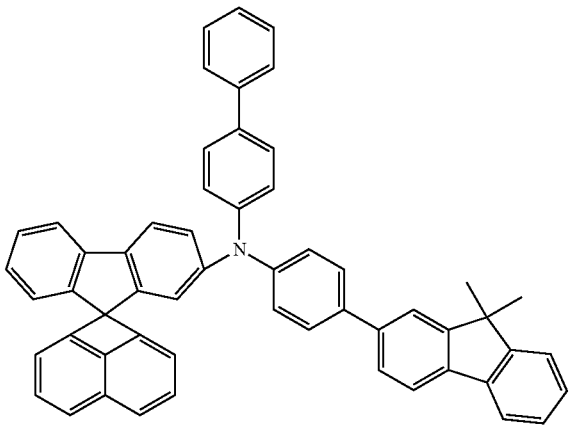

4

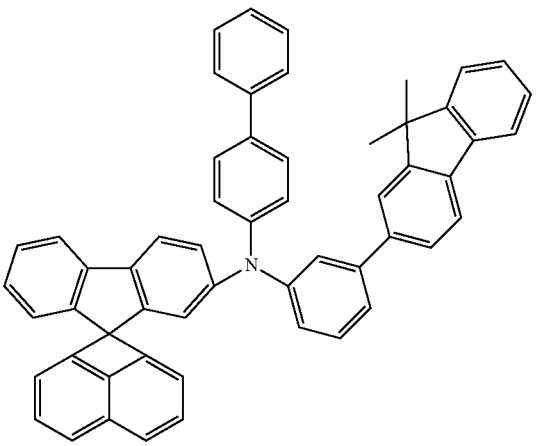

5

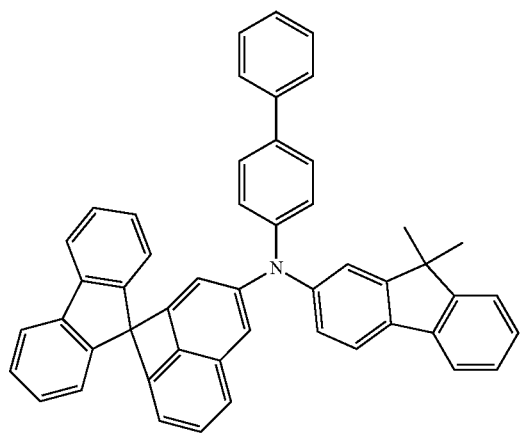

6
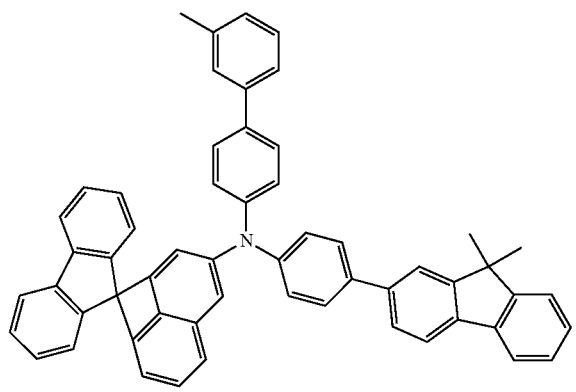
7
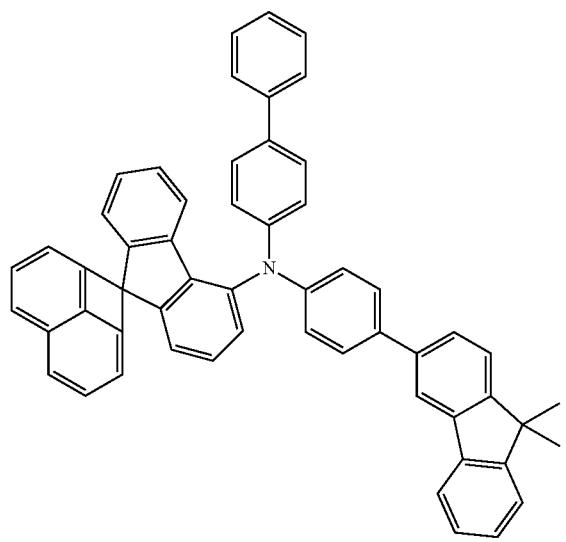
8
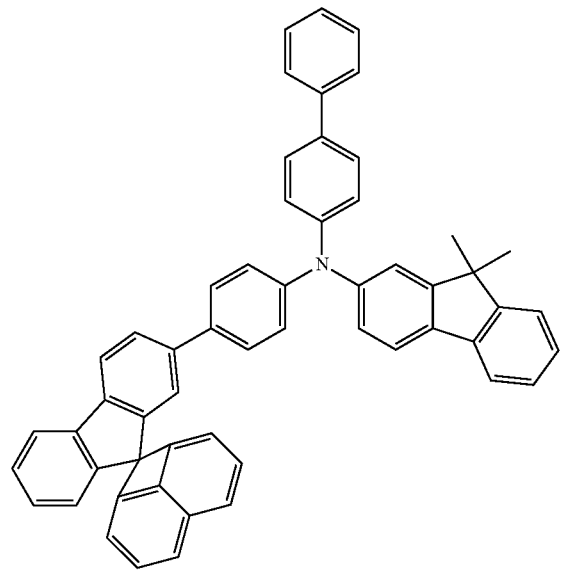
9
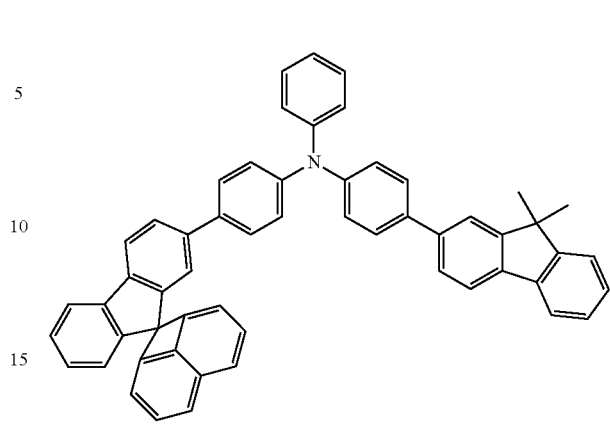
10
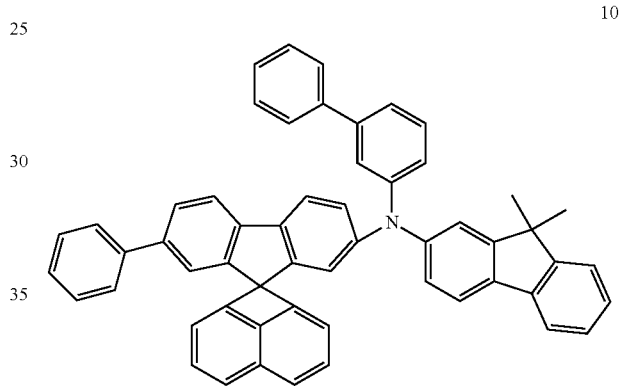
11
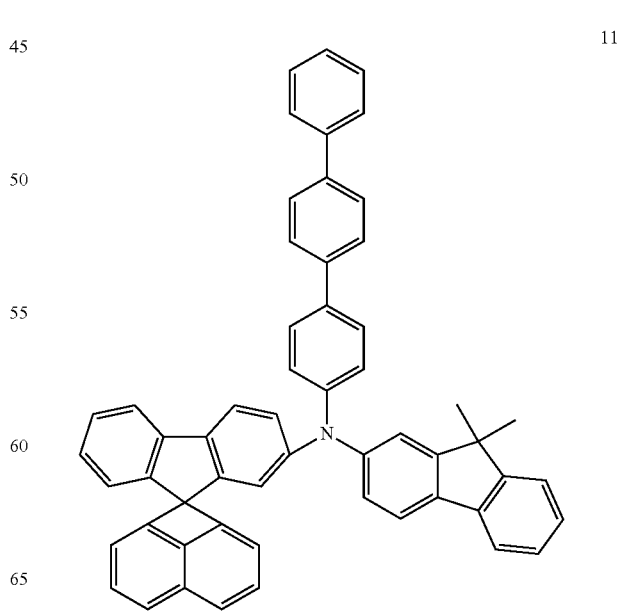

12
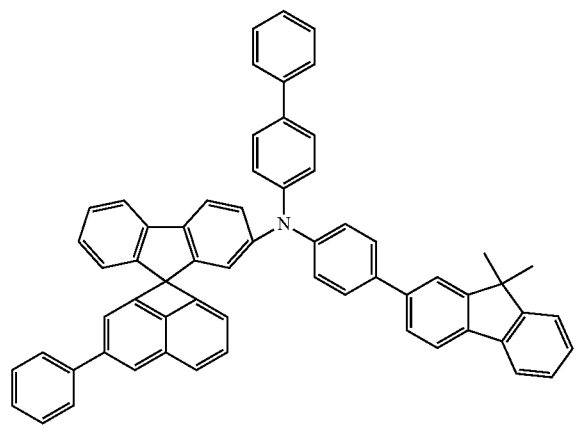
13
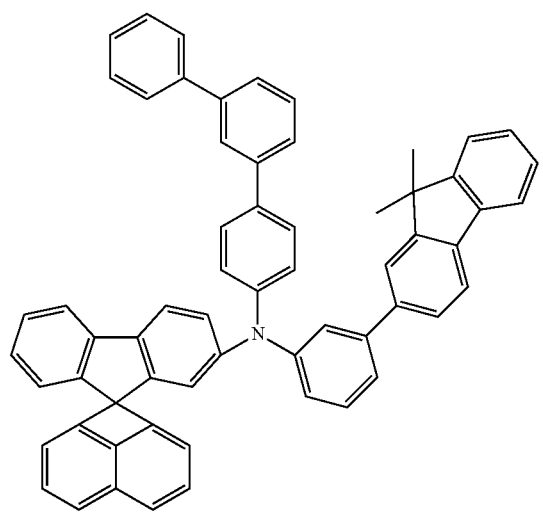
14
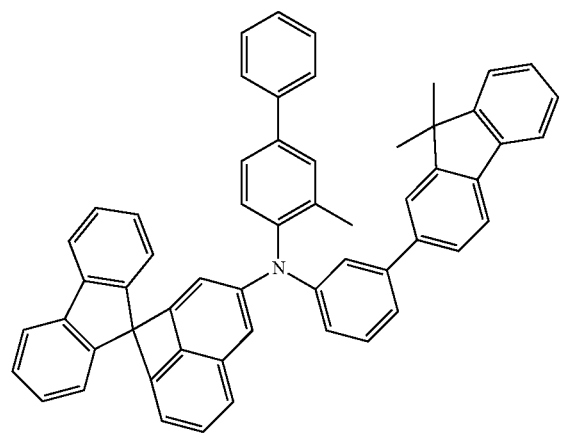
15
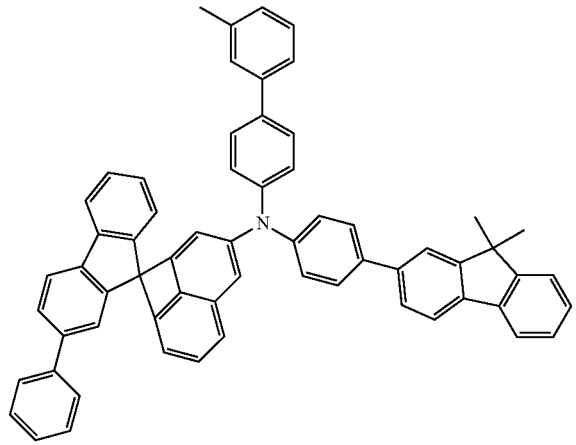
16
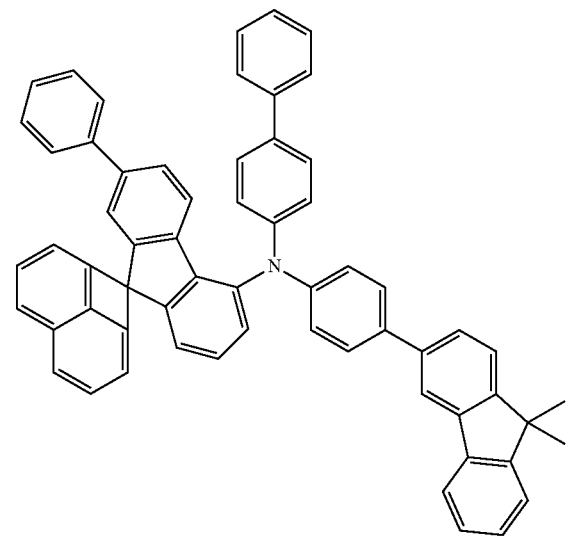
17
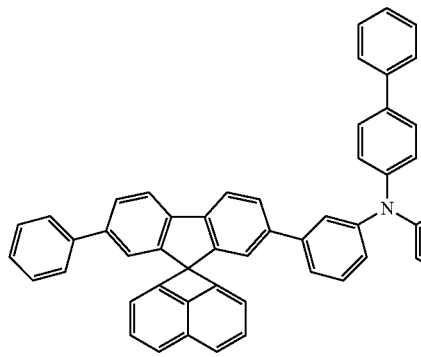

18
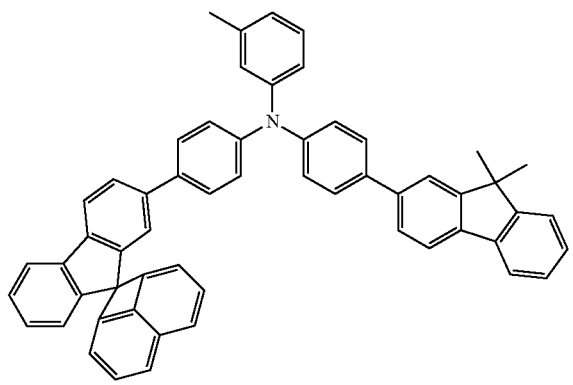
19
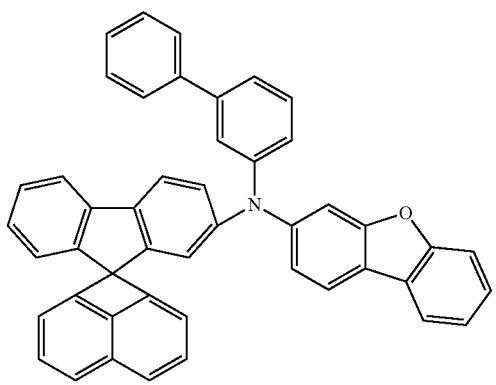
20
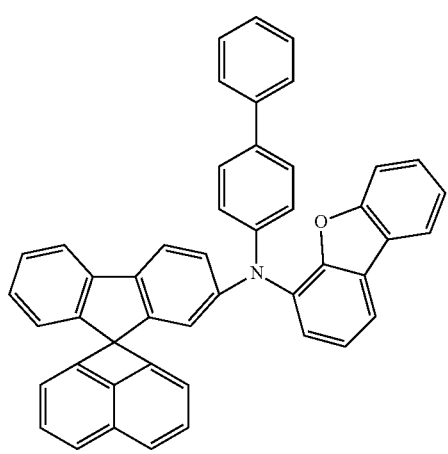
21
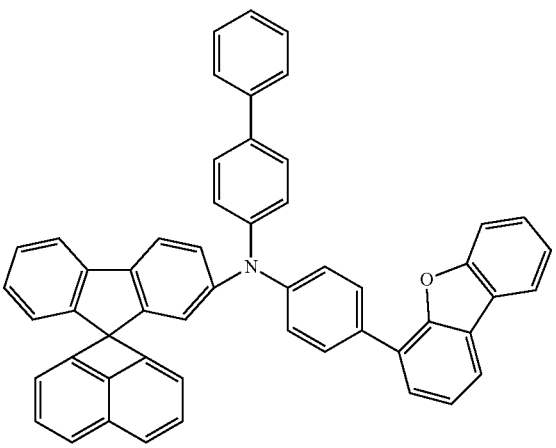
22
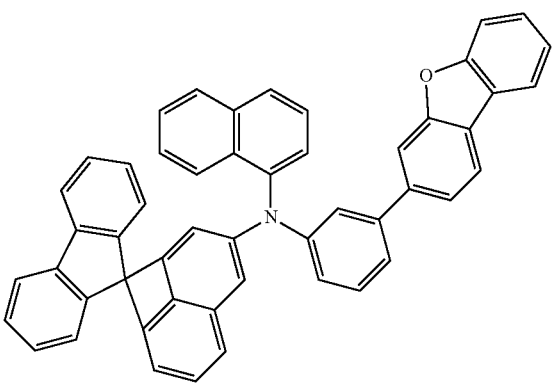
23

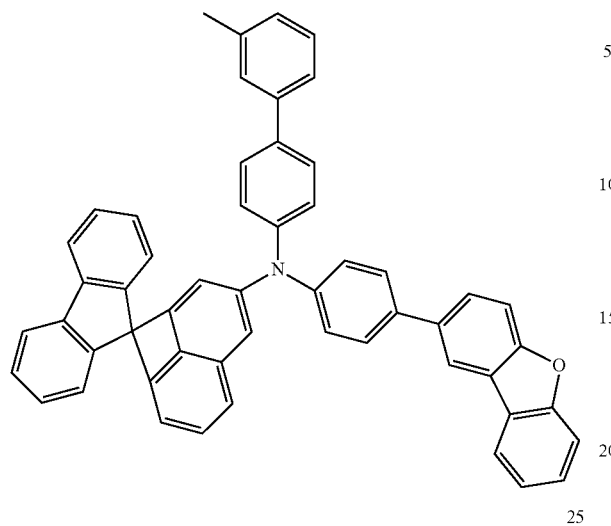
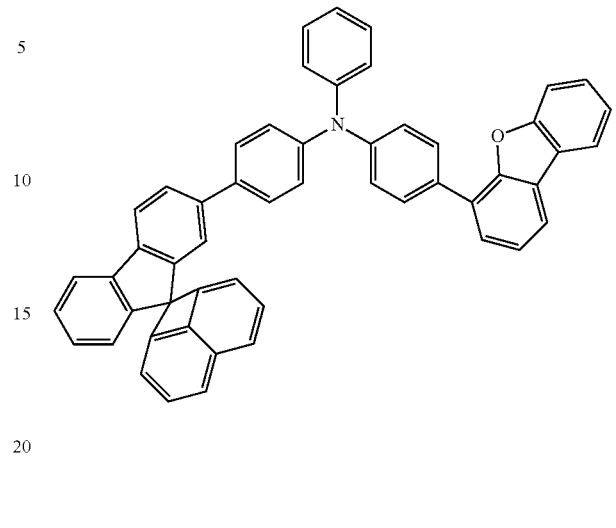
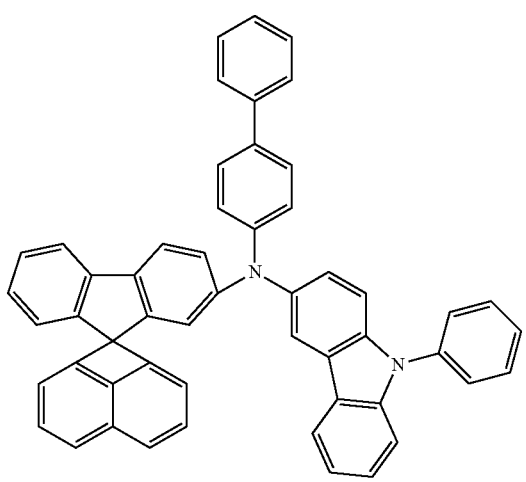
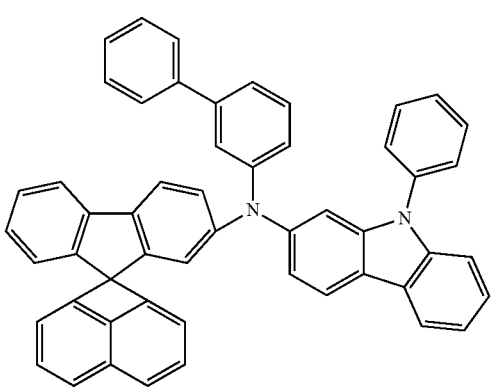

30
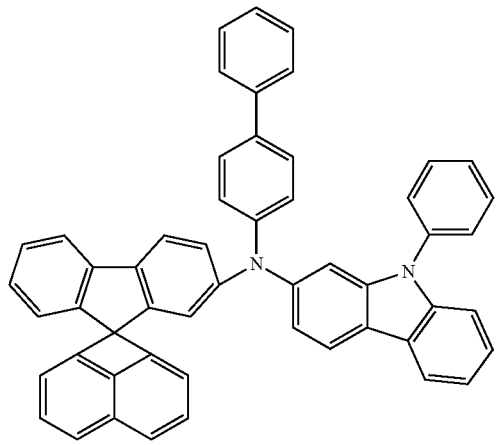
31
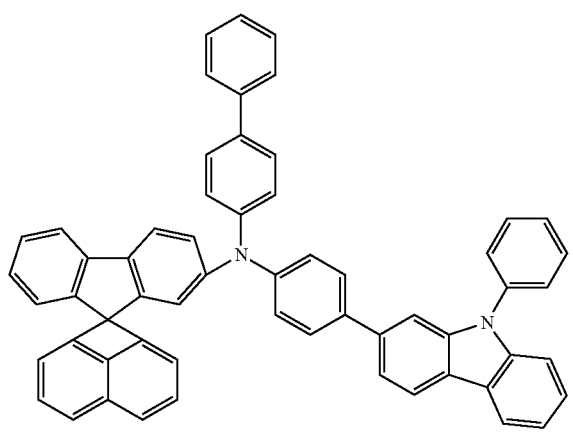
32
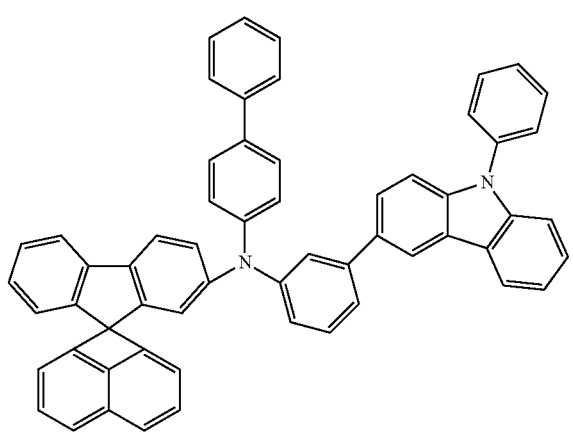
33
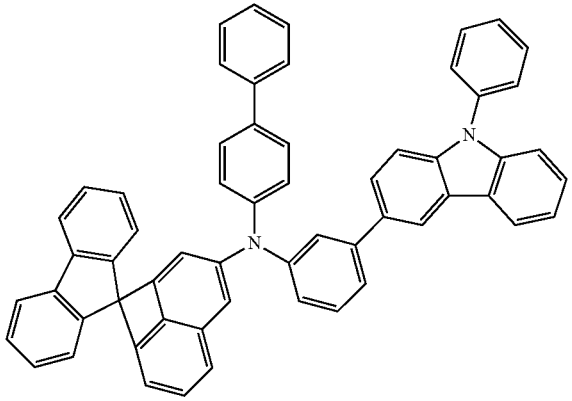
34
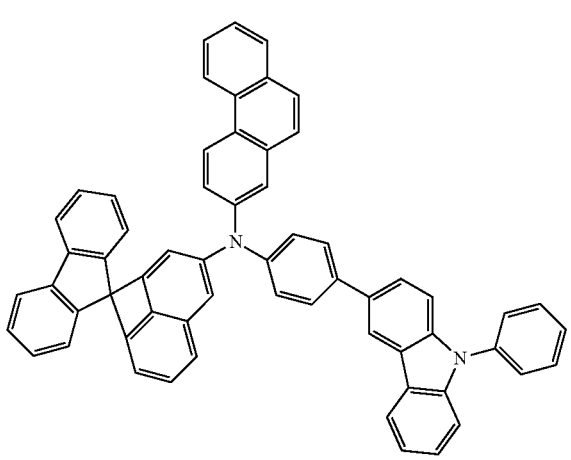
35
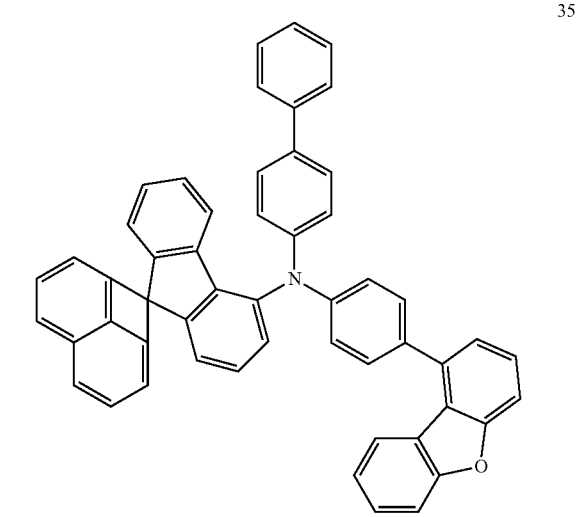

36
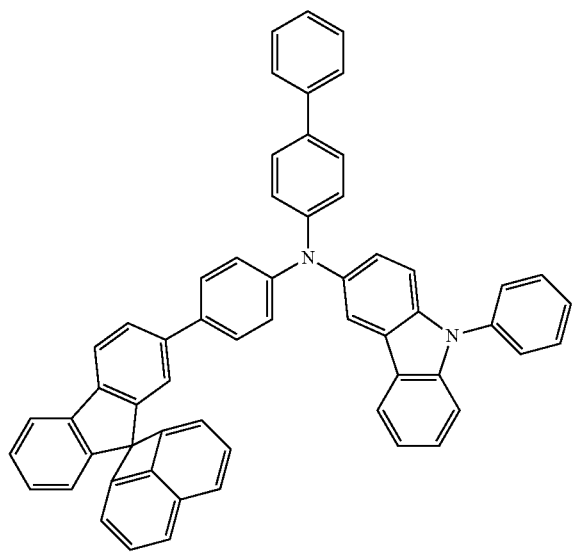
37
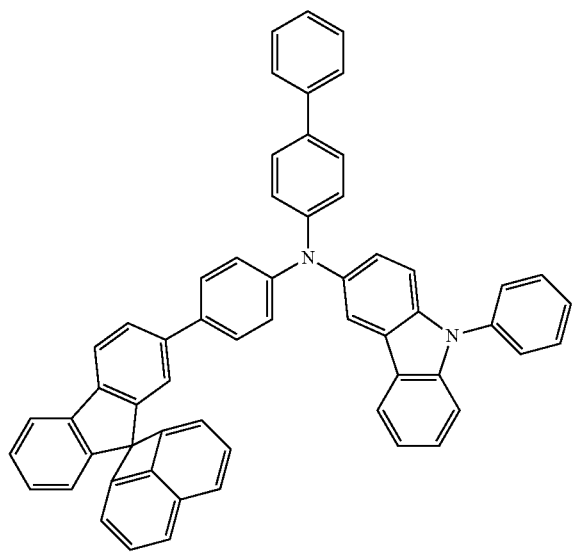
38
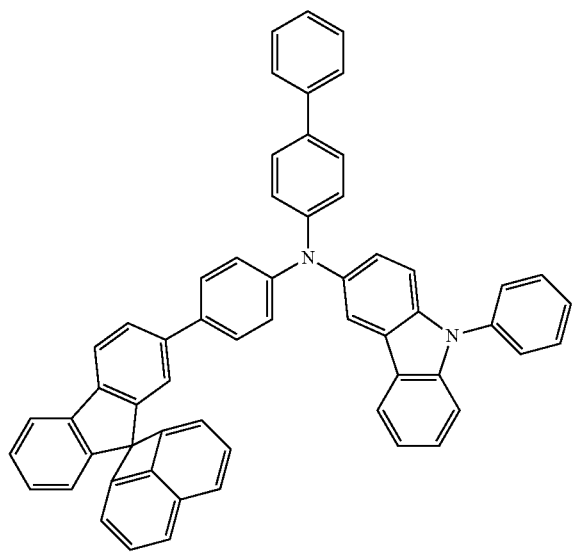
39
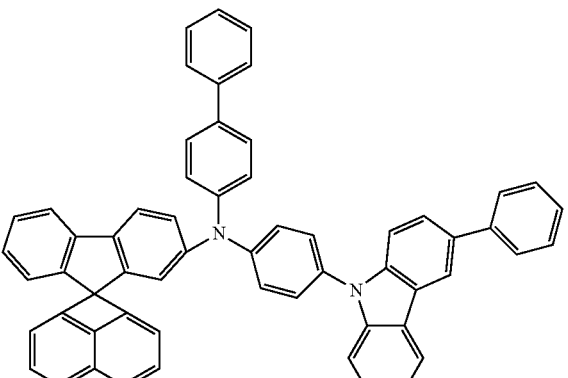
40
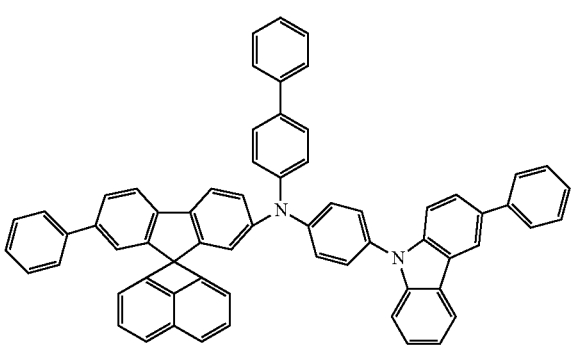
41
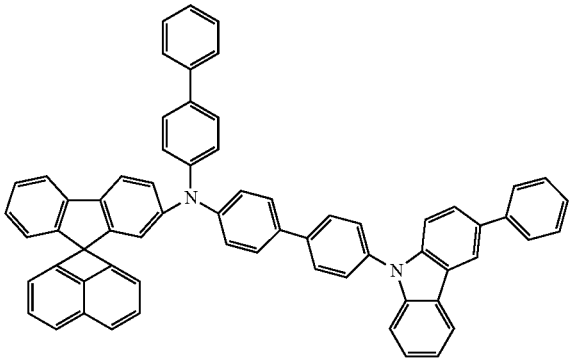
42
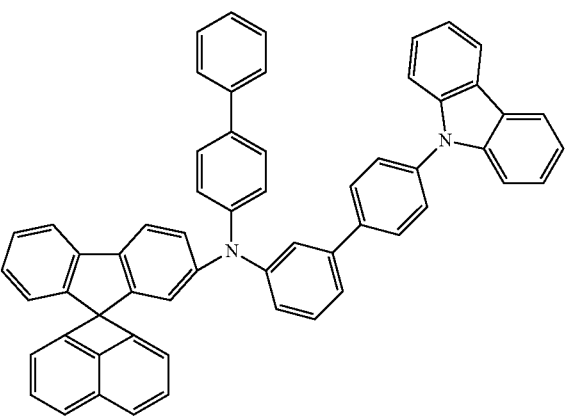

43
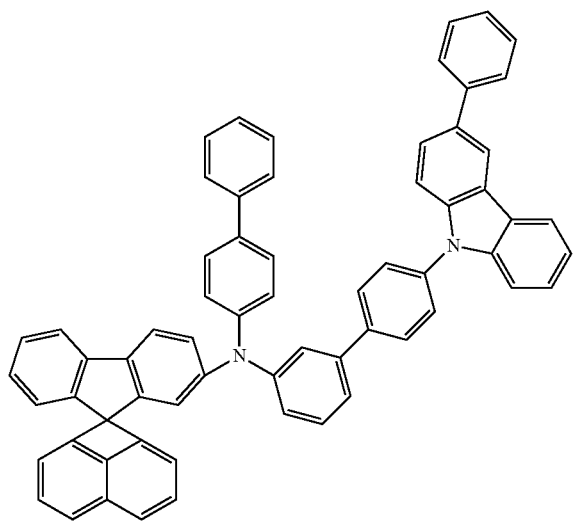
44
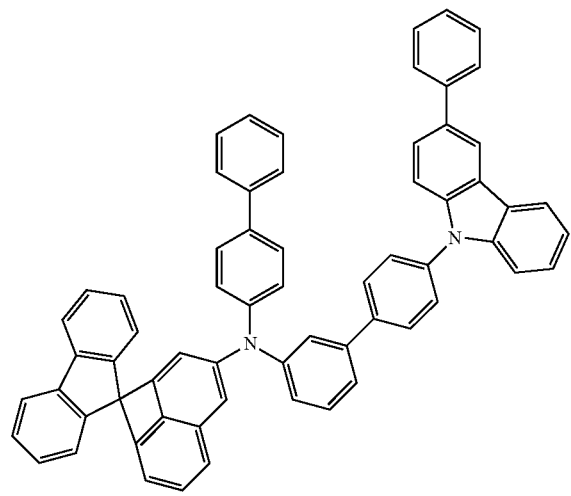
45
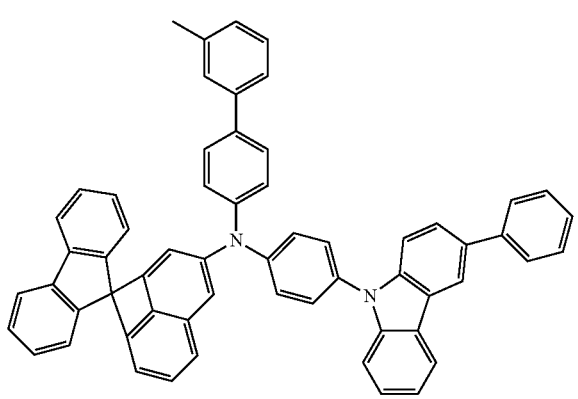
46
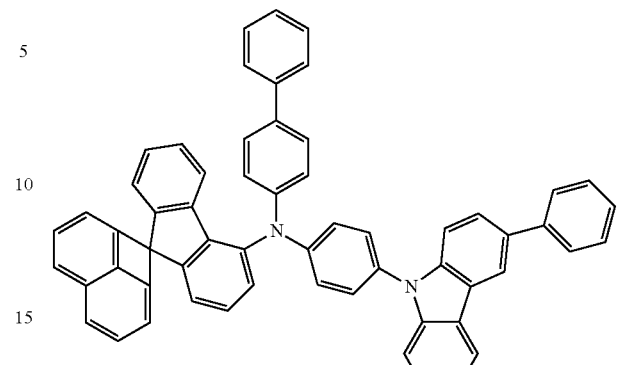
47
48
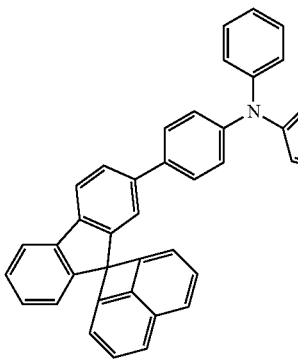

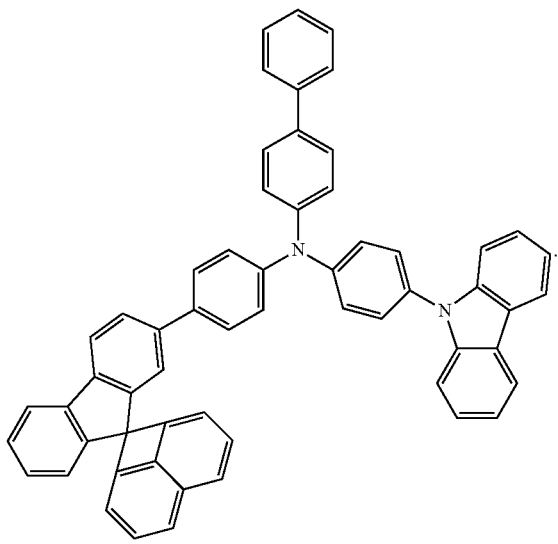

4. A material for forming a hole injection layer, a hole transport layer, an electron blocking layer or an emission layer, the material comprising the organic compound according to claim 1.

5. An organic electroluminescence device, having one or more organic thin film layers, including at least an emission layer, laminated between a cathode and an anode, wherein:
at least one of the organic thin film layers contains one or two or more of the organic compound according to claim 1.

6. An organic electroluminescence device having a hole injection layer, a hole transport layer, an emission layer, an electron transport layer, and an electron injection layer, wherein the emission layer is laminated between a cathode and an anode, and the organic compound according to claim 1 is contained in one or more of the hole injection layer, the hole transport layer, and the emission layer.

7. An organic electroluminescence device having a hole injection layer, a hole transport layer, an electron blocking layer, an emission layer, a hole blocking layer, an electron transport layer, and an electron injection layer, wherein the emission layer is laminated between a cathode and an anode, and the organic compound according to claim 1 is contained in one or more of the hole injection layer, the hole transport layer, the electron blocking layer, and the emission layer.

* * * * *